(12) United States Patent
Griffiths et al.

(10) Patent No.: US 10,555,777 B2
(45) Date of Patent: Feb. 11, 2020

(54) SYSTEM AND METHOD FOR REGISTERING TO A SURGICAL TABLE

(71) Applicant: INTUITIVE SURGICAL OPERATIONS, INC., Sunnyvale, CA (US)

(72) Inventors: Paul G. Griffiths, Santa Clara, CA (US); Brandon D. Itkowitz, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 329 days.

(21) Appl. No.: 15/522,180

(22) PCT Filed: Oct. 27, 2015

(86) PCT No.: PCT/US2015/057664
§ 371 (c)(1),
(2) Date: Apr. 26, 2017

(87) PCT Pub. No.: WO2016/069655
PCT Pub. Date: May 6, 2016

(65) Prior Publication Data
US 2018/0289427 A1 Oct. 11, 2018

Related U.S. Application Data

(60) Provisional application No. 62/134,296, filed on Mar. 17, 2015, provisional application No. 62/069,245, filed on Oct. 27, 2014.

(51) Int. Cl.
*G05B 19/18* (2006.01)
*A61B 34/20* (2016.01)
(Continued)

(52) U.S. Cl.
CPC .............. *A61B 34/20* (2016.02); *A61B 34/32* (2016.02); *A61G 13/04* (2013.01); *A61G 13/10* (2013.01);
(Continued)

(58) Field of Classification Search
CPC ......... A61B 34/20; A61B 34/32; A61B 34/30; A61B 2034/2059; A61G 13/10;
(Continued)

(56) References Cited

U.S. PATENT DOCUMENTS

| 4,625,837 A | 12/1986 | Zimmer et al. |
| 4,640,663 A | 2/1987 | Niinomi et al. |

(Continued)

FOREIGN PATENT DOCUMENTS

| CN | 2910169 Y | 6/2007 |
| CN | 101049248 A | 10/2007 |

(Continued)

OTHER PUBLICATIONS

Extended European Search Report for Application No. 15855456.8, dated Sep. 25, 2018, 10 pages.
(Continued)

*Primary Examiner* — Khoi H Tran
*Assistant Examiner* — B M M Hannan
(74) *Attorney, Agent, or Firm* — Artegis Law Group, LLP

(57) ABSTRACT

A system and method of registering a surgical table and a computer-assisted device includes an articulated arm and a control unit coupled to the articulated arm. The articulated arm has a distally mounted instrument configured to be inserted into a patient at a body opening. The control unit is configured to detect a first motion of a surgical table coupled to the control unit via a communications connection. The first motion of the surgical table causes a corresponding second motion of a control point of the articulated arm. The
(Continued)

control unit is further configured to determine a first angular direction of the first motion in a surgical table coordinate frame, determine a second angular direction of the second motion in a computer-assisted medical device coordinate frame, and determine a third angular relationship between the surgical table and the computer-assisted medical device based on the first and second angular directions.

34 Claims, 11 Drawing Sheets

(51) Int. Cl.
    *A61G 13/04*     (2006.01)
    *A61B 34/32*     (2016.01)
    *A61G 13/10*     (2006.01)

(52) U.S. Cl.
    CPC .. *A61B 2034/2059* (2016.02); *A61G 2203/36* (2013.01)

(58) Field of Classification Search
    CPC ........ A61G 13/02; A61G 13/06; A61G 13/04; A61G 2203/36
    USPC ...................................................... 700/250
    See application file for complete search history.

(56) References Cited

U.S. PATENT DOCUMENTS

| | | |
|---|---|---|
| 4,693,665 A | 9/1987 | Friederichs et al. |
| 4,894,855 A | 1/1990 | Kresse |
| 4,928,047 A | 5/1990 | Arai et al. |
| 4,945,914 A | 8/1990 | Allen |
| 5,144,213 A | 9/1992 | Sasaki et al. |
| 5,222,499 A | 6/1993 | Allen et al. |
| 5,397,323 A | 3/1995 | Taylor et al. |
| 5,784,542 A | 7/1998 | Ohm et al. |
| 5,790,307 A | 8/1998 | Mick et al. |
| 5,994,864 A | 11/1999 | Inoue et al. |
| 6,246,200 B1 | 6/2001 | Blumenkranz et al. |
| 6,471,165 B2 | 10/2002 | Twisselmann |
| 6,471,167 B1 | 10/2002 | Myers et al. |
| 6,560,492 B2 | 5/2003 | Borders |
| 7,089,612 B2 | 8/2006 | Rocher et al. |
| 7,155,315 B2 | 12/2006 | Niemeyer et al. |
| 7,189,246 B2 | 3/2007 | Otsuka et al. |
| 7,720,322 B2 | 5/2010 | Prisco et al. |
| 7,741,802 B2 | 6/2010 | Prisco et al. |
| 7,763,015 B2 | 7/2010 | Cooper et al. |
| 7,837,674 B2 | 11/2010 | Cooper |
| 7,852,030 B2 | 12/2010 | Kamiya |
| 8,004,229 B2 | 8/2011 | Nowlin et al. |
| 8,069,714 B2 | 12/2011 | Ortmaier et al. |
| 8,226,072 B2 | 7/2012 | Murayama |
| 8,271,130 B2 | 9/2012 | Hourtash |
| 8,400,094 B2 | 3/2013 | Schena |
| 8,464,720 B1 | 6/2013 | Pigazzi et al. |
| 8,541,970 B2 | 9/2013 | Nowlin et al. |
| 8,620,473 B2 | 12/2013 | Diolaiti et al. |
| 8,624,537 B2 | 1/2014 | Nowlin et al. |
| 8,641,621 B2 | 2/2014 | Razzaque et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,852,208 B2 | 10/2014 | Gomez et al. |
| 8,918,211 B2 | 12/2014 | Diolaiti et al. |
| 9,060,678 B2 | 6/2015 | Larkin et al. |
| 9,078,686 B2 | 7/2015 | Schena |
| 9,084,623 B2 | 7/2015 | Gomez et al. |
| 9,102,058 B2 | 8/2015 | Hofmann et al. |
| 9,107,683 B2 | 8/2015 | Hourtash et al. |
| 9,138,129 B2 | 9/2015 | Diolaiti |
| 9,295,524 B2 | 3/2016 | Schena et al. |
| 9,296,104 B2 | 3/2016 | Swarup et al. |
| 9,333,042 B2 | 5/2016 | Diolaiti et al. |
| 9,334,911 B2 | 5/2016 | Kameta et al. |
| 9,345,544 B2 | 5/2016 | Hourtash et al. |
| 9,375,284 B2 | 6/2016 | Hourtash |
| 9,387,593 B2 | 7/2016 | Bonin et al. |
| 9,415,510 B2 | 8/2016 | Hourtash et al. |
| 9,468,501 B2 | 10/2016 | Hourtash et al. |
| 9,469,034 B2 | 10/2016 | Diolaiti et al. |
| 9,492,235 B2 | 11/2016 | Hourtash et al. |
| 9,492,927 B2 | 11/2016 | Diolaiti et al. |
| 9,918,681 B2 | 3/2018 | Wallace et al. |
| 10,064,689 B2 | 9/2018 | Swarup et al. |
| 10,226,306 B2 | 3/2019 | Itkowitz et al. |
| 10,272,569 B2 | 4/2019 | Swarup et al. |
| 2002/0082612 A1 | 6/2002 | Moll et al. |
| 2003/0192758 A1 | 10/2003 | Murata et al. |
| 2006/0025668 A1 | 2/2006 | Peterson et al. |
| 2007/0013336 A1* | 1/2007 | Nowlin .................. B25J 9/1682 318/568.21 |
| 2007/0096670 A1 | 5/2007 | Hashimoto et al. |
| 2007/0185376 A1* | 8/2007 | Wilson .................. A61B 17/02 600/102 |
| 2007/0270685 A1* | 11/2007 | Kang ................. A61B 17/1764 600/424 |
| 2008/0004633 A1 | 1/2008 | Arata et al. |
| 2008/0046122 A1 | 2/2008 | Manzo et al. |
| 2008/0064921 A1 | 3/2008 | Larkin et al. |
| 2008/0125649 A1 | 5/2008 | Meyer et al. |
| 2008/0312529 A1 | 12/2008 | Amiot et al. |
| 2009/0088774 A1 | 4/2009 | Swarup et al. |
| 2009/0326324 A1* | 12/2009 | Munoz Martinez ... A61B 34/30 600/118 |
| 2010/0042097 A1 | 2/2010 | Newton et al. |
| 2010/0138183 A1 | 6/2010 | Jensen et al. |
| 2010/0168762 A1 | 7/2010 | Osawa et al. |
| 2010/0204713 A1 | 8/2010 | Ruiz et al. |
| 2010/0228249 A1 | 9/2010 | Mohr et al. |
| 2010/0228264 A1 | 9/2010 | Robinson et al. |
| 2010/0292843 A1 | 11/2010 | Kariyazaki et al. |
| 2011/0015521 A1 | 1/2011 | Faul |
| 2011/0071508 A1 | 3/2011 | Duval et al. |
| 2012/0029694 A1* | 2/2012 | Muller ................. A61B 6/0407 700/248 |
| 2012/0101508 A1* | 4/2012 | Wook Choi ........... B25J 9/1697 606/130 |
| 2013/0085510 A1* | 4/2013 | Stefanchik .......... G06F 19/3481 606/130 |
| 2013/0096701 A1 | 4/2013 | Suorajaervi et al. |
| 2013/0110129 A1 | 5/2013 | Reid et al. |
| 2014/0005654 A1 | 1/2014 | Batross et al. |
| 2014/0039517 A1 | 2/2014 | Bowling et al. |
| 2014/0052153 A1 | 2/2014 | Griffiths et al. |
| 2014/0052154 A1 | 2/2014 | Griffiths et al. |
| 2014/0055489 A1 | 2/2014 | Itkowitz et al. |
| 2014/0222207 A1 | 8/2014 | Bowling et al. |
| 2014/0276887 A1 | 9/2014 | Stein et al. |
| 2014/0305995 A1 | 10/2014 | Shelton, IV et al. |
| 2014/0316430 A1 | 10/2014 | Hourtash et al. |
| 2014/0358161 A1 | 12/2014 | Hourtash et al. |
| 2015/0032126 A1 | 1/2015 | Nowlin et al. |
| 2015/0051733 A1 | 2/2015 | Nowlin et al. |
| 2015/0150639 A1 | 6/2015 | Diolaiti et al. |
| 2015/0224845 A1 | 8/2015 | Anderson et al. |
| 2016/0081754 A1 | 3/2016 | Kostrzewski et al. |
| 2017/0079722 A1 | 3/2017 | O'Grady et al. |
| 2017/0079730 A1 | 3/2017 | Azizian et al. |
| 2017/0079731 A1 | 3/2017 | Griffiths et al. |
| 2017/0086932 A1 | 3/2017 | Auld et al. |
| 2017/0112580 A1 | 4/2017 | Griffiths et al. |
| 2017/0312047 A1 | 11/2017 | Swarup et al. |
| 2017/0333141 A1 | 11/2017 | Itkowitz et al. |
| 2017/0333142 A1 | 11/2017 | Itkowitz et al. |
| 2017/0333145 A1 | 11/2017 | Griffiths et al. |
| 2017/0333275 A1 | 11/2017 | Itkowitz et al. |
| 2017/0334067 A1 | 11/2017 | Swarup et al. |

(56) References Cited

U.S. PATENT DOCUMENTS

| | | |
|---|---|---|
| 2018/0338808 A1 | 11/2018 | Swarup et al. |
| 2019/0142533 A1 | 5/2019 | Itkowitz et al. |
| 2019/0176327 A1 | 6/2019 | Swarup et al. |

FOREIGN PATENT DOCUMENTS

| | | | |
|---|---|---|---|
| CN | 101217913 | A | 7/2008 |
| CN | 201082167 | Y | 7/2008 |
| CN | 101332137 | A | 12/2008 |
| CN | 101466342 | A | 6/2009 |
| CN | 101472546 | A | 7/2009 |
| CN | 101959656 | A | 1/2011 |
| CN | 102046360 | A | 5/2011 |
| CN | 101443163 | B | 8/2011 |
| CN | 101234033 | B | 6/2012 |
| CN | 103221015 | A | 7/2013 |
| CN | 104002296 | B | 5/2016 |
| EP | 1915963 | A1 | 4/2008 |
| EP | 2047805 | A1 | 4/2009 |
| EP | 2332477 | A2 | 6/2011 |
| EP | 2332479 | A2 | 6/2011 |
| EP | 2332482 | A2 | 6/2011 |
| JP | H06278063 | A | 10/1994 |
| JP | H0884735 | A | 4/1996 |
| JP | H09300264 | A | 11/1997 |
| JP | 2000107200 | A | 4/2000 |
| JP | 2004216022 | A | 8/2004 |
| JP | 2010194101 | A | 9/2010 |
| JP | 2011212837 | A | 10/2011 |
| JP | 2012005557 | A | 1/2012 |
| WO | WO-2006039092 | A2 | 4/2006 |
| WO | WO-2006069288 | A2 | 6/2006 |
| WO | WO-2006124390 | A2 | 11/2006 |
| WO | WO-2007136770 | A2 | 11/2007 |
| WO | WO-2008002830 | A2 | 1/2008 |
| WO | WO-2011109041 | A1 | 9/2011 |
| WO | WO-2013048957 | A1 | 4/2013 |
| WO | WO-2013181503 | A1 | 12/2013 |
| WO | WO-2013181507 | A1 | 12/2013 |
| WO | WO-2013181516 | A1 | 12/2013 |
| WO | WO-2014028703 | A1 | 2/2014 |
| WO | WO-2014146095 | A1 | 9/2014 |
| WO | WO-2014146107 | A1 | 9/2014 |
| WO | WO-2014146113 | A1 | 9/2014 |
| WO | WO-2014146119 | A1 | 9/2014 |
| WO | WO-2014146120 | A1 | 9/2014 |
| WO | WO-2015142798 | A1 | 9/2015 |
| WO | WO-2015142930 | A1 | 9/2015 |
| WO | WO-2015142943 | A1 | 9/2015 |
| WO | WO-2015142947 | A1 | 9/2015 |
| WO | WO-2016069648 | A1 | 5/2016 |
| WO | WO-2016069659 | A1 | 5/2016 |
| WO | WO-2016069660 | A1 | 5/2016 |
| WO | WO-2016069661 | A1 | 5/2016 |
| WO | WO-2016069663 | A1 | 5/2016 |

OTHER PUBLICATIONS

Co-pending U.S. Appl. No. 61/954,120, filed Mar. 17, 2014.
International Search Report and Written Opinion for Application No. PCT/US2015/057656, dated Feb. 1, 2016, 11 pages.
International Search Report and Written Opinion for Application No. PCT/US2015/057658, dated Feb. 1, 2016, 12 pages.
International Search Report and Written Opinion for Application No. PCT/US2015/057664, dated Feb. 1, 2016, 8 pages.
International Search Report and Written Opinion for Application No. PCT/US2015/057669, dated Feb. 1, 2016, 9 pages.
International Search Report and Written Opinion for Application No. PCT/US2015/057670, dated Feb. 2016, 8 pages.
International Search Report and Written Opinion for Application No. PCT/US2015/057671, dated Feb. 1, 2016, 6 pages.
International Search Report and Written Opinion for Application No. PCT/US2015/057673, dated Feb. 1, 2016, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15855051.7, dated May 3, 2018, 10 pages.
Extended European Search Report for Application No. EP15855097, dated Apr. 25, 2018, 11 pages.
Extended European Search Report for Application No. EP15855351.1, dated Apr. 30, 2018, 9 pages.
Extended European Search Report for Application No. EP15854253, dated May 11, 2018, 11 pages.
Partial Supplementary European Search Report for Application No. EP15855456.8, dated May 23, 2018, 11 pages.
Extended European Search Report for Application No. EP15854136.7, dated Jun. 7, 2018, 11 pages.
Extended European Search Report for Application No. EP15854260.5, dated Jun. 7, 2018, 8 pages.
Hesse S., et al., "Lexikon Der Elektrischen Antriebstechnik," Festo Didactic GmbH & Co. KG, Jan. 1, 2004, pp. 1-198, XP055260002 [retrieved on Mar. 21, 2016], Retrieved from the Internet:< url:http://www.boss.festo-cpx.com/pdf/539265_webprint.pdf">.

* cited by examiner

SYSTEM AND METHOD FOR REGISTERING TO A SURGICAL TABLE

RELATED APPLICATIONS

This application is a U.S. National Stage patent application of International Patent Application No. PCT/US2015/057664 (filed on Oct. 27 2015), the benefit of which is claimed, and claims priority to U.S. Provisional Patent Application No. 62/069,245 entitled "System and Method for Integrated Operating Table," which was filed Oct. 27, 2014, and U.S. Provisional Patent Application No. 62/134,296 entitled "System and Method for Registering to a Surgical Table," which was filed on Mar. 17, 2015, each of which are hereby incorporated by reference in their entirety.

TECHNICAL FIELD

The present disclosure relates generally to operation of devices with articulated arms and more particularly to determining registration between a device with the articulated arms and an integrated surgical table.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices. As more and more autonomous and semiautonomous devices are placed in use it opens opportunities where two or more of the devices cooperate to achieve a common goal.

Consider, for example, a scenario in an operating room or interventional suite where a computer-assisted surgical device with one or more articulated arms is being used to perform a procedure on a patient located on a surgical table having an articulated structure that allows the top of the surgical table to move. When a surgeon and/or other operating room staff want to readjust and/or move the patient using the surgical table, this movement occurs relative to the articulated arms of the computer-assisted surgical device. To avoid causing injury to the patient, damage to the computer-assisted device, and/or damage to the surgical table it is desirable for the computer-assisted surgical device to detect the motion in the surgical table and adjust the articulated arms accordingly. In order to do this effectively, it is often helpful to know the geometric and/or kinematic relationship between the surgical table and the computer-assisted surgical device. One solution to the problem is to have operating room staff manually enter the position and orientation. In practice this may be a cumbersome, impractical, and/or error-prone procedure. Other solutions involve placing the computer-assisted surgical device at a known position and orientation relative to the surgical table, such as by bolting the computer-assisted surgical device to the surgical table and/or using an articulated structure between the computer-assisted surgical device and the surgical table that may be used to determine the position and orientation of the computer-assisted surgical device and the surgical table. Both of these approaches may unreasonably restrict possible positions and orientations of the computer-assisted surgical device that may make it difficult for the computer-assisted surgical device to be effectively used on patients of various sizes and/or for different types of procedures. In addition, these approaches may introduce additional steps that may have to be performed when the computer-assisted surgical device and/surgical table is moved.

Accordingly, it would be advantageous to have improved systems and methods that determine the position and orientation (i.e., registration) of a computer-assisted surgical device and surgical table.

SUMMARY

Consistent with some embodiments, a computer-assisted medical device includes an articulated arm and a control unit coupled to the articulated arm. The articulated arm has a distally mounted instrument configured to be inserted into a patient at a body opening. The control unit is configured to detect a first motion of a surgical table coupled to the control unit via a communications connection. The first motion of the surgical table causes a corresponding second motion of a control point of the articulated arm. The control unit is further configured to determine a first angular direction of the first motion in a surgical table coordinate frame, determine a second angular direction of the second motion in a computer-assisted medical device coordinate frame, and determine a third angular relationship between the surgical table and the computer-assisted medical device based on the first and second angular directions.

According to some embodiments, the control unit is further configured to detect a third motion of the surgical table. The third motion of the surgical table includes a first rotation about a first axis. The third motion of the surgical table causes a corresponding fourth motion of the control point. The control unit is further configured to detect a fifth motion of the surgical table. The fifth motion of the surgical table includes a second rotation about a second axis. The fifth motion of the surgical table causes a corresponding sixth motion of the control point. The second axis is different than the first axis. The control unit is further configured to determine a first perpendicular distance between the control point and the first axis based on the first rotation and the fourth motion of the control point, determine a second perpendicular distance between the control point and the second axis based on the second rotation and the sixth motion of the control point, and determine an XY registration between the device and the surgical table based on a position of the control point and the first and second perpendicular distances.

Consistent with some embodiments, a method of registering a surgical table and a computer-assisted medical device includes detecting a first motion of a surgical table. The first motion causes a corresponding second motion of a control point of an articulated arm of the computer-assisted medical device. The computer-assisted medical device is coupled to the surgical table via a communications connection. The method further includes determining a first angular direction of the first motion in a surgical table coordinate frame, determining a second angular direction of the second motion in a computer-assisted medical device coordinate frame, and determining a third angular relationship between the surgical table and the computer-assisted medical device based on the first and second angular directions.

According to some embodiments, the method further includes detecting a third motion of the surgical table. The third motion of the surgical table includes a first rotation about a first axis. The third motion of the surgical table causes a corresponding fourth motion of the control point. The method further includes detecting a fifth motion of the surgical table. The fifth motion of the surgical table includes a second rotation about a second axis. The fifth motion of the surgical table causes a corresponding sixth motion of the control point. The second axis is different than the first axis. The method further includes determining a first perpendicular distance between the control point and the first axis based on the first rotation and the fourth motion of the control point, determining a second perpendicular distance between the control point and the second axis based on the second rotation and the sixth motion of the control point, and determining an XY registration between the device and the surgical table based on a position of the control point and the first and second perpendicular distances.

Consistent with some embodiments, a non-transitory machine-readable medium includes a plurality of machine-readable instructions which when executed by one or more processors associated with a computer-assisted medical device are adapted to cause the one or more processors to perform a method. The method includes detecting a first motion of a surgical table. The first motion causes a corresponding second motion of a control point of an articulated arm of the computer-assisted medical device. The computer-assisted medical device is coupled to the surgical table via a communications connection. The method further includes determining a first angular direction of the first motion in a surgical table coordinate frame, determining a second angular direction of the second motion in a computer-assisted medical device coordinate frame, and determining a third angular relationship between the surgical table and the computer-assisted medical device based on the first and second angular directions.

According to some embodiments, the method further includes detecting a third motion of the surgical table. The third motion of the surgical table includes a first rotation about a first axis. The third motion of the surgical table causes a corresponding fourth motion of the control point. The method further includes detecting a fifth motion of the surgical table. The fifth motion of the surgical table includes a second rotation about a second axis. The fifth motion of the surgical table causes a corresponding sixth motion of the control point. The second axis is different than the first axis. The method further includes determining a first perpendicular distance between the control point and the first axis based on the first rotation and the fourth motion of the control point, determining a second perpendicular distance between the control point and the second axis based on the second rotation and the sixth motion of the control point, and determining an XY registration between the device and the surgical table based on a position of the control point and the first and second perpendicular distances.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
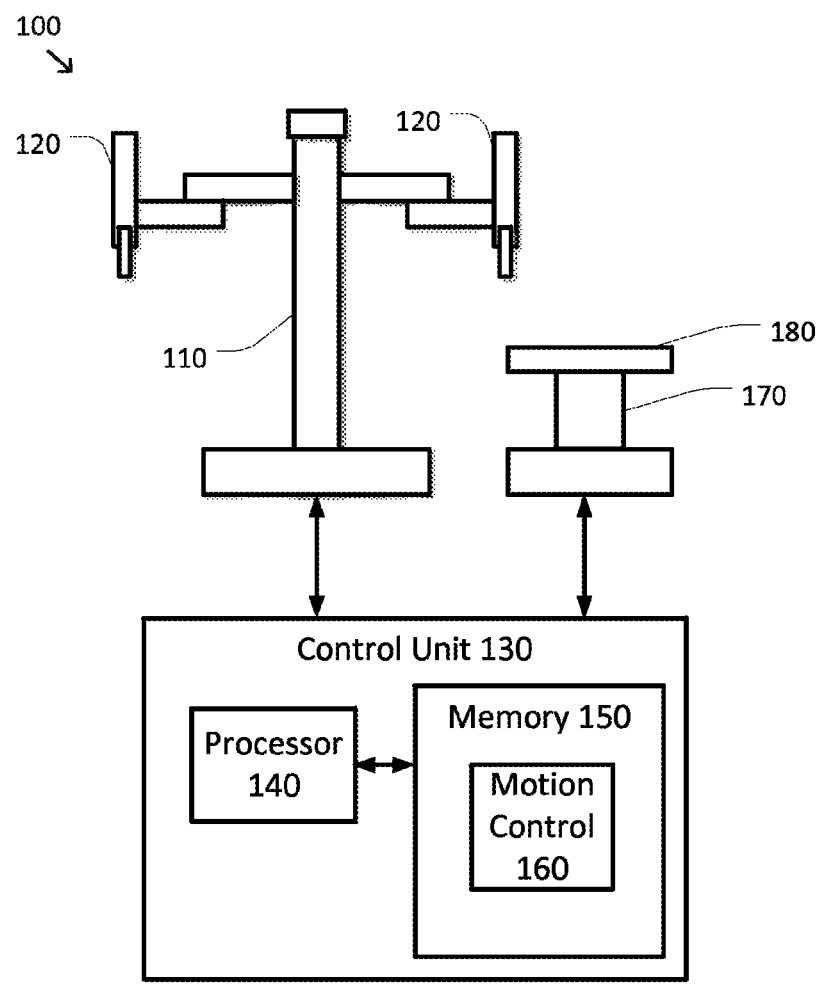
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a device 110 with one or more movable or articulated arms 120. Each of the one or more articulated arms 120 supports one or more end effectors. In some examples, device 110 may be consistent with a computer-assisted surgical device. The one or more articulated arms 120 each provides support for one or more instruments, surgical instruments, imaging devices, and/or the like mounted to a distal end of at least one of the articulated arms 120. Device 110 may further be coupled to an operator workstation (not shown), which may include one or more master controls for operating the device 110, the one or more articulated arms 120, and/or the end effectors. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may optionally be used with computer-assisted system 100.

Device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 is used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that supports autonomous and/or semiautonomous control of device 110. Motion control application 160 may include one or more application programming interfaces (APIs) for receiving position, motion, and/or other sensor information from device 110, exchanging position, motion, and/or collision avoidance information with other control units regarding other devices, such as a surgical table and/or imaging device, and/or planning and/or assisting in the planning of motion for device 110, articulated arms 120, and/or the end effectors of device 110. And although motion control application 160 is depicted as a software application, motion control application 160 may be implemented using hardware, software, and/or a combination of hardware and software.

In some embodiments, computer-assisted system 100 may be found in an operating room and/or an interventional suite. And although computer-assisted system 100 includes only one device 110 with two articulated arms 120, one of ordinary skill would understand that computer-assisted system 100 may include any number of devices with articulated arms and/or end effectors of similar and/or different design from device 110. In some examples, each of the devices may include fewer or more articulated arms and/or end effectors.

Computer-assisted system 100 further includes a surgical table 170. Like the one or more articulated arms 120, surgical table 170 supports articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a surgical table command unit for controlling the position and/or orientation of table top 180. In some embodiments, surgical table 170 may correspond to one or more of the surgical tables commercialized by Trumpf Medical Systems GmbH of Germany.

Surgical table 170 is also coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, motion control application 160 may include one or more application programming interfaces (APIs) for receiving position, motion, and/or other sensor information associated with surgical table 170 and/or table top 180. In some examples, motion control application 160 may plan and/or assist in the planning of motion for surgical table 170 and/or table top 180. In some examples, motion control application 160 may contribute to motion plans associated with collision avoidance, adapting to and/or avoid range of motion limits in joints and links, movement of articulated arms, instruments, end effectors, surgical table components, and/or the like to compensate for other motion in the articulated arms, instruments, end effectors, surgical table components, and/or the like, adjust a viewing device such as an endoscope to maintain and/or place an area of interest and/or one or more instruments or end effectors within a field of view of the viewing device. In some examples, motion control application 160 may prevent motion of surgical table 170 and/or table top 180, such as by preventing movement of surgical table 170 and/or table top 180 through use of the surgical table command unit. In some examples, motion control application 160 may help register device 110 with surgical table 170 so that a geometric relationship between device 110 and surgical table 170 is known. In some examples, the geometric relationship may include a translation and/or one or more rotations between coordinate frames maintained for device 110 and surgical table 170.

Figure 2:
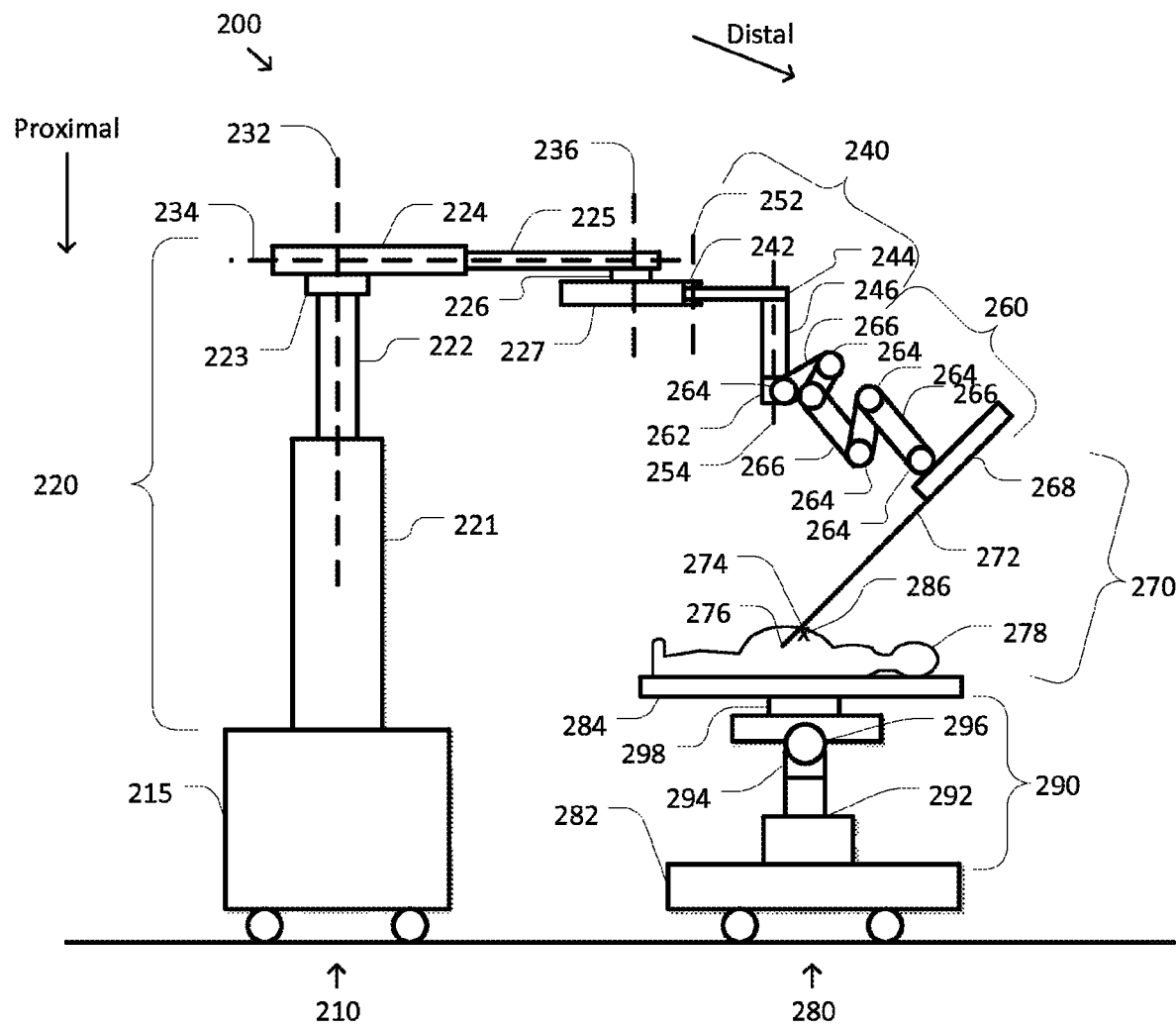
FIG. 2 is a simplified diagram showing a computer-assisted system according to some embodiments.

FIG. 2 is a simplified diagram showing a computer-assisted system 200 according to some embodiments. For example, the computer-assisted system 200 may be consistent with computer-assisted system 100. As shown in FIG. 2, the computer-assisted system 200 includes a computer-assisted device 210 with one or more articulated arms and a surgical table 280. Although not shown in FIG. 2, the computer-assisted device 210 and the surgical table 280 are coupled together using one or more interfaces and one or more control units so that at least kinematic information about the surgical table 280 is known to the motion control application being used to perform motion of the articulated arms of the computer-assisted device 210.

The computer-assisted device 210 includes various links and joints. In the embodiments of FIG. 2, the computer-assisted device is generally divided into three different sets of links and joints. Starting at the proximal end with a mobile cart 215 or patient-side cart 215 is a set-up structure 220. Coupled to a distal end of the set-up structure is a series of links and set-up joints 240 forming an articulated arm. And coupled to a distal end of the set-up joints 240 is a multi jointed manipulator 260. In some examples, the series of set-up joints 240 and manipulator 260 may correspond to one of the articulated arms 120. And although the computer-assisted device is shown with only one series of set-up joints 240 and a corresponding manipulator 260, one of ordinary skill would understand that the computer-assisted device may include more than one series of set-up joints 240 and corresponding manipulators 260 so that the computer-assisted device is equipped with multiple articulated arms.

As shown, the computer-assisted device 210 is mounted on the mobile cart 215. The mobile cart 215 enables the computer-assisted device 210 to be transported from location to location, such as between operating rooms or within an operating room to better position the computer-assisted device in proximity to the surgical table 280. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is adjusted along an axis 234 using the two-part boom. And the orientation of the arm mounting platform 227 may also adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may also be adjusted radially and angularly about the mobile cart 215 using the two-part boom and the shoulder joint 223, respectively. And the angular orientation of the arm mounting platform 227 may also be changed using the wrist joint 226.

The arm mounting platform 227 is used as a mounting point for one or more articulated arms. The ability to adjust the height, horizontal position, and orientation of the arm mounting platform 227 about the mobile cart 215 provides a flexible set-up structure for positioning and orienting the one or more articulated arms about a work space located near the mobile cart 215 where an operation or procedure is to take place. For example, arm mounting platform 227 may be positioned above a patient so that the various articulated arms and their corresponding manipulators and instruments have sufficient range of motion to perform a surgical procedure on the patient. FIG. 2 shows a single articulated arm coupled to the arm mounting platform 227 using a first set-up joint 242. And although only one articulated arm is shown, one of ordinary skill would understand that multiple articulated arms may be coupled to the arm mounting platform 227 using additional first set-up joints.

The first set-up joint 242 forms the most proximal portion of the set-up joints 240 section of the articulated arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to the arm mounting platform 227 along an axis 254, and rotate the manipulator mount 262 about axis 254. In some examples, the set-up joints 240 may further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument 270 is mounted to the instrument carriage 268. Instrument 270 includes a shaft 272, which is aligned along an insertion axis. The shaft 272 is typically aligned so that it passes through a remote center of motion 274 associated with the manipulator 260. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relationship of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety In some examples, the remote center of motion 274 may correspond to a location of a body opening, such as an incision site or body orifice, in a patient 278 where shaft 272 is inserted into the patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be optionally passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or the end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with manipulators for use with the da Vinci® Surgical System commercialized by Intuitive Surgical, Inc. of Sunnyvale, Calif. In some examples, the instrument 270 may be an imaging device such as an endoscope, a gripper, a surgical instrument such as a cautery or a scalpel, and/or the like. In some examples, the end effector 276 may include additional degrees of freedom, such as roll, pitch, yaw, grip, and/or the like that allow for additional localized manipulation of portions of the end effector 276 relative to the distal end of the shaft 272.

During a surgery or other medical procedure, the patient 278 is typically located on the surgical table 280. The surgical table 280 includes a table base 282 and a table top 284, with the table base 282 being located in proximity to mobile cart 215 so that the instrument 270 and/or end effector 276 may be manipulated by the computer-assisted device 210 while the shaft 272 of instrument 270 is inserted into the patient 278 at the body opening. The surgical table 280 further includes an articulated structure 290 that includes one or more joints or links between the table base 282 and the table top 284 so that the relative location of the table top 284, and thus the patient 278, relative to the table base 282 is controlled. In some examples, the articulated structure 290 may be configured so that the table top 284 is controlled relative to a virtually-defined table motion isocenter 286 that may be located at a point above the table top 284. In some examples, isocenter 286 may be located within the interior of the patient 278. In some examples, isocenter 286 may be collocated with the body wall of the patient at or near one of the body openings, such as a body opening site corresponding to remote center of motion 274.

As shown in FIG. 2, the articulated structure 290 includes a height adjustment joint 292 so that the table top 284 may be raised and/or lowered relative to the table base 282. The articulated structure 290 further includes joints and links to change both the tilt 294 and Trendelenburg 296 orientation of the table top 284 relative to the isocenter 286. The tilt 294 allows the table top 284 to be tilted side-to-side so that either the right or left side of the patient 278 is rotated upward relative to the other side of the patient 278 (i.e., about a longitudinal or head-to-toe (cranial-caudal) axis of the table top 284). The Trendelenburg 296 allows the table top 284 to be rotated so that either the feet of the patient 278 are raised (Trendelenburg) or the head of the patient 278 is raised (reverse Trendelenburg). In some examples, either the tilt 294 and/or the Trendelenburg 296 rotations may be adjusted to generate rotations about isocenter 286. The articulated structure 290 further includes additional links and joints 298 to slide the table top 284 along the longitudinal (cranial-caudal) axis relative to the table base 282 with generally a left and/or right motion as depicted in FIG. 2.

FIGS. 8A-8G are simplified schematic views that illustrate various computer-assisted system architectures that incorporate the integrated computer-assisted device and movable surgical table features described herein. The various illustrated system components are in accordance with the principles described herein. In these illustrations, the components are simplified for clarity, and various details such as individual links, joints, manipulators, instruments, end effectors, etc. are not shown, but they should be understood to be incorporated in the various illustrated components.

In these architectures, cannulas associated with one or more surgical instruments or clusters of instruments are not shown, and it should be understood that cannulas and other instrument guide devices optionally may be used for instruments or instrument clusters having a relatively larger shaft or guide tube outer diameter (e.g., 4-5 mm or more) and optionally may be omitted for instruments having a relatively smaller shaft or guide tube outer diameter (e.g., 2-3 mm or less).

Also in these architectures, teleoperated manipulators should be understood to include manipulators that during surgery define a remote center of motion by using hardware constraints (e.g., fixed intersecting instrument pitch, yaw, and roll axes) or software constraints (e.g., software-constrained intersecting instrument pitch, yaw, and roll axes). A hybrid of such instrument axes of rotation may be defined (e.g., hardware-constrained roll axis and software-constrained pitch and yaw axes) are also possible. Further, some manipulators may not define and constrain any surgical instrument axes of rotation during a procedure, and some manipulators may define and constrain only one or two instrument axes of rotation during a procedure.

Figure 8A:
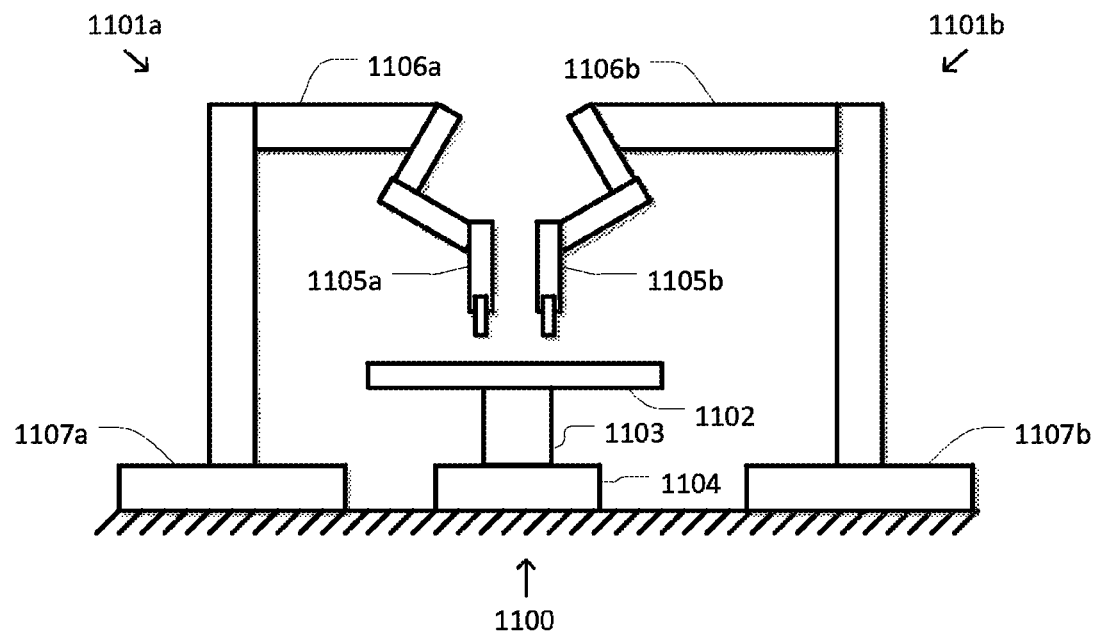
FIGS. 8A-8G are simplified schematic views that illustrate various computer-assisted system architectures that incorporate the integrated computer-assisted device and movable surgical table features described herein.

FIG. 8A illustrates a movable surgical table 1100 and a single-instrument computer-assisted device 1101a are shown. Surgical table 1100 includes a movable table top 1102 and a table support structure 1103 that extends from a mechanically grounded table base 1104 to support the table top 1102 at a distal end. In some examples, surgical table 1100 may be consistent with surgical table 170 and/or 280. Computer-assisted device 1101a includes a teleoperated manipulator and a single instrument assembly 1105a. Computer-assisted device 1101a also includes a support structure 1106a that is mechanically grounded at a proximal base 1107a and that extends to support manipulator and instrument assembly 1105a at a distal end. Support structure 1106a is configured to allow assembly 1105a to be moved and held in various fixed poses with reference to surgical table 1100. Base 1107a is optionally permanently fixed or movable with reference to surgical table 1100. Surgical table 1100 and computer-assisted device 1101a operate together as described herein.

FIG. 8A further shows an optional second computer-assisted device 1101b, which illustrates that two, three, four, five, or more individual computer-assisted devices may be included, each having a corresponding individual teleoperated manipulator and single-instrument assembly(ies) 1105b supported by a corresponding support structure 1106b. Computer-assisted device 1101b is mechanically grounded, and assemblies 1105b are posed, similarly to computer-assisted device 1101a. Surgical table 1100 and computer-assisted devices 1101a and 1101b together make a multi-instrument surgical system, and they operate together as described herein. In some examples, computer-assisted devices 1101a and/or 1101b may be consistent with computer-assisted devices 110 and/or 210.

Figure 8B:
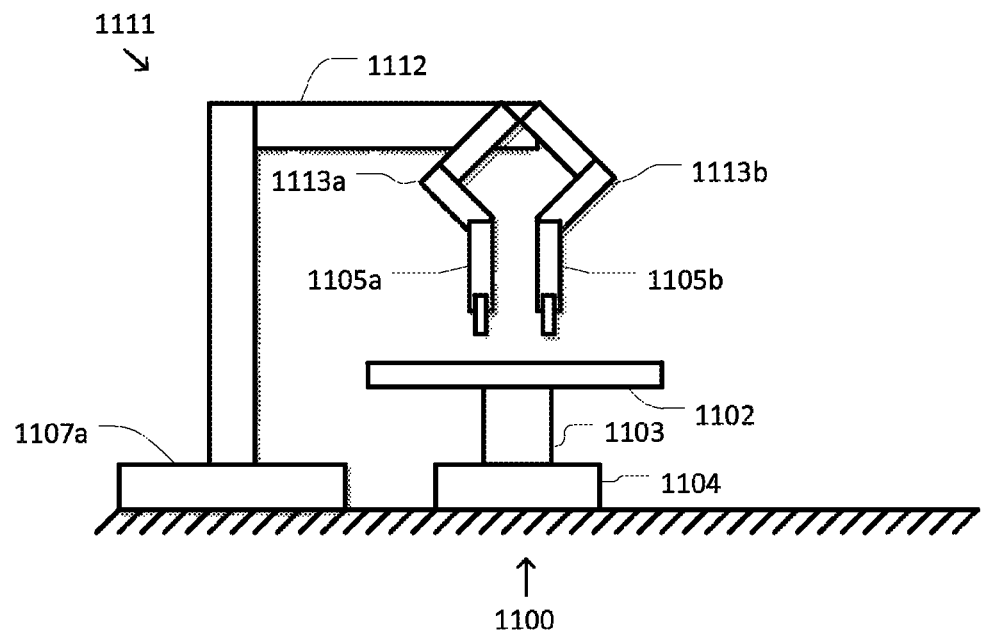

As shown in FIG. 8B, another movable surgical table 1100 and a computer-assisted device 1111 are shown. Computer-assisted device 1111 is a multi-instrument device that includes two, three, four, five, or more individual teleoperated manipulator and single-instrument assemblies as shown by representative manipulator and instrument assemblies 1105a and 1105b. The assemblies 1105a and 1105b of computer-assisted device 1111 are supported by a combined support structure 1112, which allows assemblies 1105a and 1105b to be moved and posed together as a group with reference to surgical table 1100. The assemblies 1105a and 1105b of computer-assisted device 1111 are also each supported by a corresponding individual support structure 1113a and 1113b, respectively, which allows each assembly 1105a and 1105b to be individually moved and posed with reference to surgical table 1100 and to the one or more other assemblies 1105a and 1105b. Examples of such a multi-instrument surgical system architecture are the da Vinci Si® Surgical System and the da Vinci® Xi™ Surgical System, commercialized by Intuitive Surgical, Inc. Surgical table 1100 and a surgical manipulator system comprising an example computer-assisted device 1111 operate together as described herein. In some examples, computer-assisted device 1111 is consistent with computer-assisted devices 110 and/or 210.

Figure 8C:
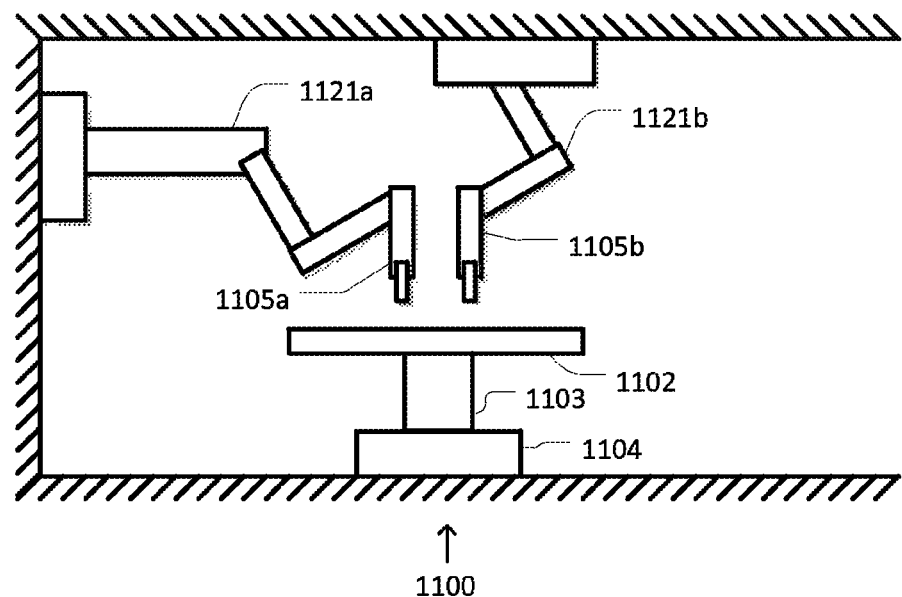

The computer-assisted devices of FIGS. 8A and 8B are each shown mechanically grounded at the floor. But, one or more such computer-assisted devices may optionally be mechanically grounded at a wall or ceiling and be permanently fixed or movable with reference to such a wall or ceiling ground. In some examples, computer-assisted devices may be mounted to the wall or ceiling using a track or grid system that allows the support base of the computer-assisted systems to be moved relative to the surgical table. In some examples, one or more fixed or releasable mounting clamps may be used to mount the respective support bases to the track or grid system. As shown in FIG. 8C, a computer-assisted device 1121a is mechanically grounded at a wall, and a computer-assisted device 1121b is mechanically grounded at a ceiling.

Figure 8D:
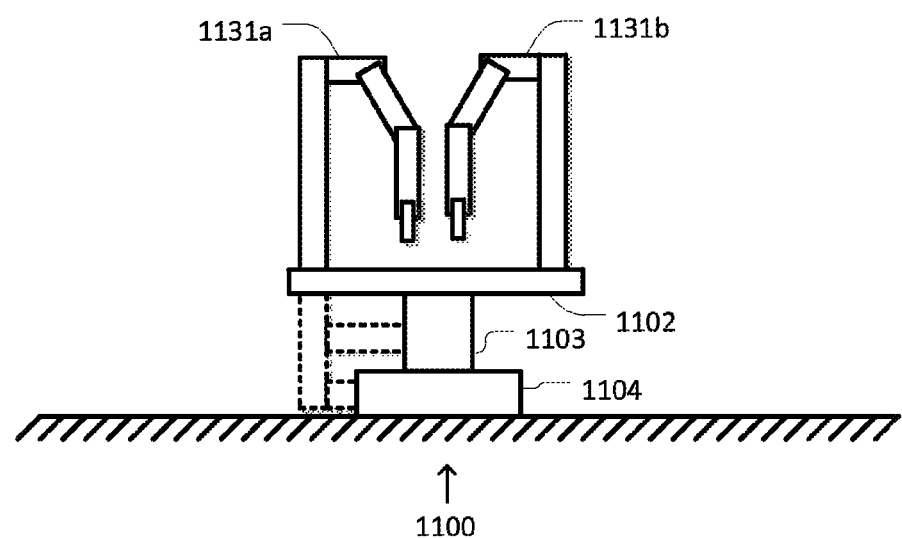

In addition, computer-assisted devices may be indirectly mechanically grounded via the movable surgical table 1100. As shown in FIG. 8D, a computer-assisted device 1131a is coupled to the table top 1102 of surgical table 1100. Computer-assisted device 1131a may optionally be coupled to other portions of surgical table 1100, such as table support structure 1103 or table base 1104, as indicated by the dashed structures shown in FIG. 8D. When table top 1102 moves with reference to table support structure 1103 or table base 1104, the computer-assisted device 1131a likewise moves with reference to table support structure 1103 or table base 1104. When computer-assisted device 1131a is coupled to table support structure 1103 or table base 1104, however, the base of computer-assisted device 1131a remains fixed with reference to ground as table top 1102 moves. As table motion occurs, the body opening where instruments are inserted into the patient may move as well because the patient's body may move and change the body opening locations relative to the table top 1102. Therefore, for embodiments in which computer-assisted device 1131a is coupled to the table top 1102, the table top 1102 functions as a local mechanical ground, and the body openings move with reference to the table top 1102, and so with reference to the computer-assisted device 1131a as well. FIG. 8D also shows that a second computer-assisted device 1131b optionally may be added, configured similarly to computer-assisted device 1131a to create a multi-instrument system. Systems that include one or more computer-assisted device coupled to the surgical table operate as disclosed herein.

In some embodiments, other combinations of computer-assisted devices with the same or hybrid mechanical groundings are possible. For example, a system may include one computer-assisted device mechanically grounded at the floor, and a second computer-assisted device mechanically grounded to the floor via the surgical table. Such hybrid mechanical ground systems operate as disclosed herein.

Figure 8E:
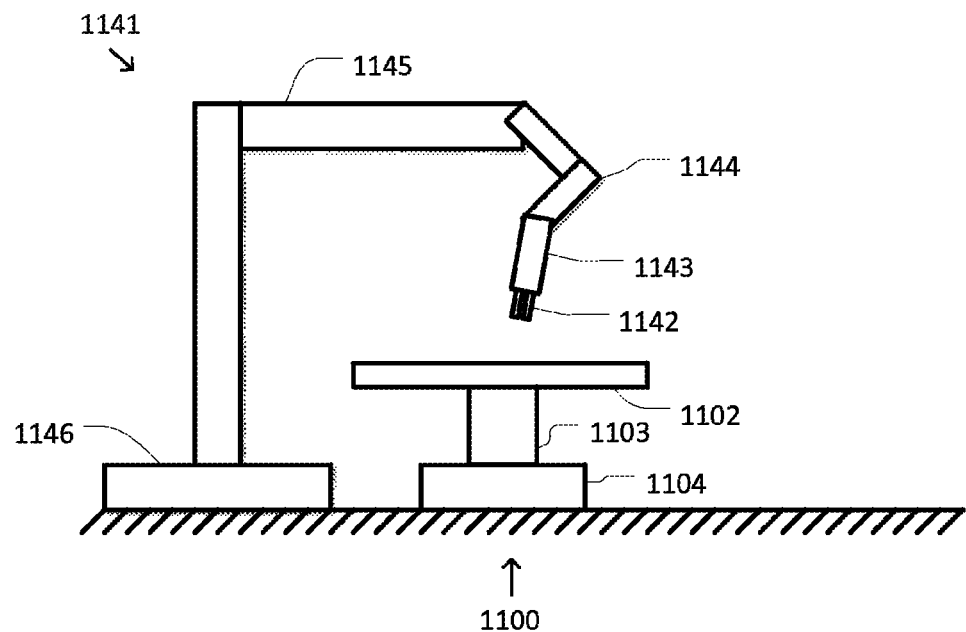

Inventive aspects also include single-body opening systems in which two or more surgical instruments enter the body via a single body opening. Examples of such systems are shown in U.S. Pat. No. 8,852,208 entitled "Surgical System Instrument Mounting," which was filed Aug. 12, 2010, and U.S. Pat. No. 9,060,678 entitled "Minimally Invasive Surgical System," which was filed Jun. 13, 2007, both of which are incorporated by reference. FIG. 8E illustrates a teleoperated multi-instrument computer-assisted device 1141 together with surgical table 1100 as described above. Two or more instruments 1142 are each coupled to a corresponding manipulator 1143 and the cluster of instruments 1142 and instrument manipulators 1143 are moved together by a system manipulator 1144. The system manipulator 1144 is supported by a support assembly 1145 that allows system manipulator 1144 to be moved to and fixed at various poses. Support assembly 1145 is mechanically grounded at a base 1146 consistent with the descriptions above. The two or more instruments 1142 are inserted into the patient at the single body opening. Optionally, the instruments 1142 extend together through a single guide tube, and the guide tube optionally extends through a cannula, as described in the references cited above. Computer-assisted device 1141 and surgical table 1100 operate together as described herein.

Figure 8F:
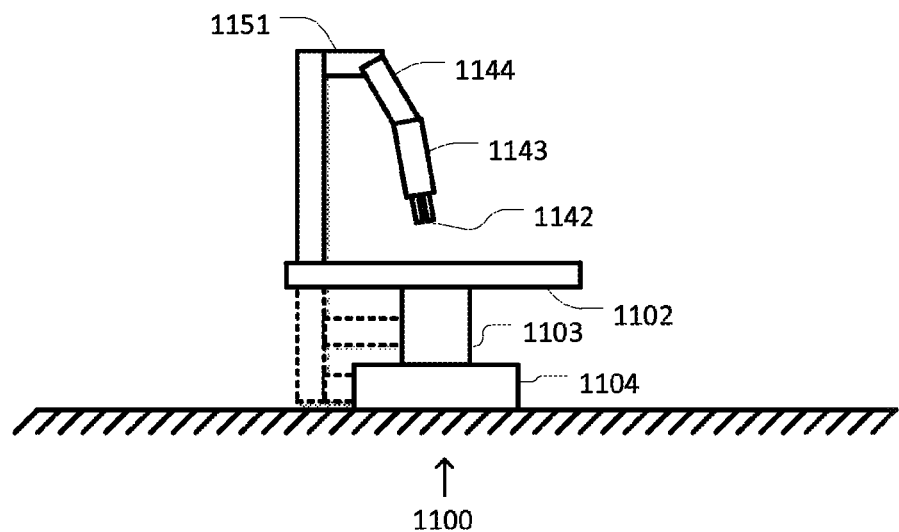

FIG. 8F illustrates another multi-instrument, single-body opening computer-assisted device 1151 mechanically grounded via the surgical table 1100, optionally by being coupled to table top 1102, table support structure 1103, or table base 1104. The descriptions above with reference to FIG. 8D also applies to the mechanical grounding options illustrated in FIG. 8F. Computer-assisted device 1151 and surgical table 1100 work together as described herein.

Figure 8G:
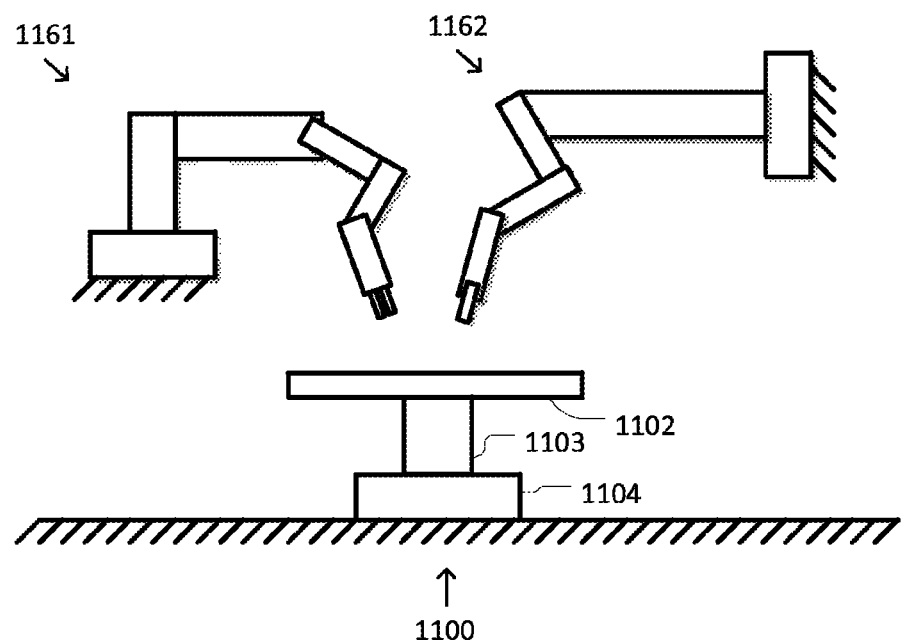

FIG. 8G illustrates that one or more teleoperated multi-instrument, single-body opening computer-assisted devices 1161 and one or more teleoperated single-instrument computer-assisted devices 1162 may be combined to operate with surgical table 1100 as described herein. Each of the computer-assisted devices 1161 and 1162 may be mechanically grounded, directly or via another structure, in various ways as described above.

Figure 3:
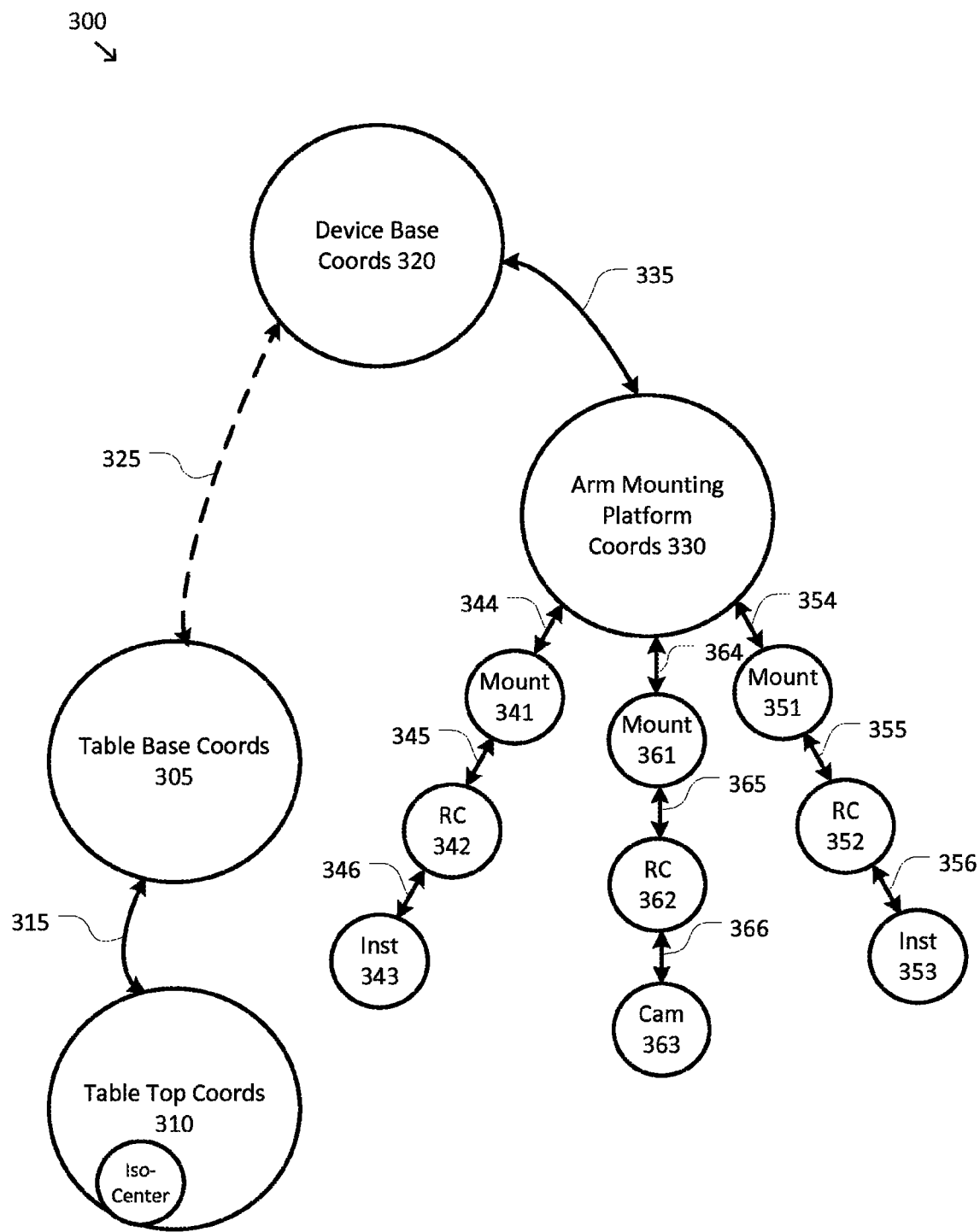
FIG. 3 is a simplified diagram of a kinematic model of a computer-assisted medical system according to some embodiments.

FIG. 3 is a simplified diagram of a kinematic model 300 of a computer-assisted medical system according to some embodiments. As shown in FIG. 3, kinematic model 300 may include kinematic information associated with many sources and/or devices. The kinematic information is based on known kinematic models for the links and joints of a computer-assisted medical device and a surgical table. The kinematic information is further based on information associated with the position and/or orientation of the joints of the computer-assisted medical device and the surgical table. In some examples, the information associated with the position and/or orientation of the joints may be derived from one or more sensors, such as encoders, measuring the linear positions of prismatic joints and the rotational positions of revolute joints.

The kinematic model 300 includes several coordinate frames or coordinate systems and transformations, such as homogeneous transforms, for transforming positions and/or orientation from one of the coordinate frames to another of the coordinate frames. In some examples, the kinematic model 300 may be used to permit the forward and/or reverse mapping of positions and/or orientations in one of the coordinate frames in any other of the coordinate frames by composing the forward and/or reverse/inverse transforms noted by the transform linkages included in FIG. 3. In some examples, when the transforms are modeled as homogenous transforms in matrix form, the composing is accomplished using matrix multiplication. In some embodiments, the kinematic model 300 may be used to model the kinematic relationships of the computer-assisted device 210 and the surgical table 280 of FIG. 2.

The kinematic model 300 includes a table base coordinate frame 305 that is used to model a position and/or orientation of a surgical table, such as surgical table 170 and/or surgical table 280. In some examples, the table base coordinate frame 305 may be used to model other points on the surgical table relative to a reference point and/or orientation associated with the surgical table. In some examples, the reference point and/or orientation may be associated with a table base of the surgical table, such as the table base 282. In some examples, the table base coordinate frame 305 may be suitable for use as a world coordinate frame for the computer-assisted system.

The kinematic model 300 further includes a table top coordinate frame 310 that may be used to model positions and/or orientations in a coordinate frame representative of a table top of the surgical table, such as the table top 284. In some examples, the table top coordinate frame 310 may be centered about a rotational center or isocenter of the table top, such as isocenter 286. In some examples, the z-axis of the table top coordinate frame 310 may be oriented vertically with respect to a floor or surface on which the surgical table is placed and/or orthogonal to the surface of the table top. In some examples, the x- and y-axes of the table top coordinate frame 310 may be oriented to capture the longitudinal (head to toe) and lateral (side-to-side) major axes of the table top. In some examples, a table base to table top coordinate transform 315 is used to map positions and/or orientations between the table top coordinate frame 310 and the table base coordinate frame 305. In some examples, one or more kinematic models of an articulated structure of the surgical table, such as articulated structure 290, along with past and/or current joint sensor readings is used to determine the table base to table top coordinate transform 315. In some examples consistent with the embodiments of FIG. 2, the table base to table top coordinate transform 315 models the composite effect of the height, tilt, Trendelenburg, and/or slide settings associated with the surgical table.

The kinematic model 300 further includes a device base coordinate frame that is used to model a position and/or orientation of a computer-assisted device, such as computer-assisted device 110 and/or computer-assisted device 210. In some examples, the device base coordinate frame 320 may be used to model other points on the computer-assisted device relative to a reference point and/or orientation associated with the computer-assisted device. In some examples, the reference point and/or orientation may be associated with a device base of the computer-assisted device, such as the mobile cart 215. In some examples, the device base coordinate frame 320 may be suitable for use as the world coordinate frame for the computer-assisted system.

In order to track positional and/or orientational relationships between the surgical table and the computer-assisted device, it is often desirable to perform a registration between the surgical table and the computer-assisted device. As shown in FIG. 3, the registration may be used to determine a registration transform 325 between the table top coordinate frame 310 and the device base coordinate from 320. In some embodiments, the registration transform 325 may be a partial or full transform between the table top coordinate frame 310 and the device base coordinate frame 320. The registration transform 325 is determined based on the architectural arrangements between the surgical table and the computer-assisted device.

In the examples of FIGS. 8D and 8F, where the computer-assisted device is mounted to the table top 1102, the registration transform 325 is determined from the table base to table top coordinate transform 315 and knowing where the computer-assisted device is mounted to the table top 112.

In the examples of FIGS. 8A-8C, 8E, and 8F, where the computer-assisted device is placed on the floor or mounted to the wall or ceiling, determination of the registration transform 325 is simplified by placing some restrictions on the device base coordinate frame 320 and the table base coordinate frame 305. In some examples, these restrictions include that both the device base coordinate frame 320 and the table base coordinate frame 305 agree on the same vertical up or z-axis. Under the assumption that the surgical table is located on a level floor, the relative orientations of the walls of the room (e.g., perpendicular to the floor) and the ceiling (e.g., parallel to the floor) are known it is possible for a common vertical up or z axis (or a suitable orientation transform) to be maintained for both the device base coordinate frame 320 and the table base coordinate frame 305 or a suitable orientation transform. In some examples, because of the common z-axis, the registration transform 325 may optionally model just the rotational relationship of the device base to the table base about the z-axis of the table base coordinate frame 305 (e.g., a $\theta_Z$ registration). In some examples, the registration transform 325 may optionally also model a horizontal offset between the table base coordinate frame 305 and the device base coordinate frame 320 (e.g., a XY registration). This is possible because the vertical (z) relationship between the computer-assisted device and the surgical table are known. Thus, changes in a height of the table top in the table base to table top transform 315 are analogous to vertical adjustments in the device base coordinate frame 320 because the vertical axes in the table base coordinate frame 305 and the device base coordinate frame 320 are the same or nearly the same so that changes in height between the table base coordinate frame 305 and the device base coordinate frame 320 are within a reasonable tolerance of each other. In some examples, the tilt and Trendelenburg adjustments in the table base to table top transform 315 may be mapped to the device base coordinate frame 320 by knowing the height of the table top (or its isocenter) and the $\theta_Z$ and/or XY registration. In some examples, the registration transform 325 and the table base to table top transform 315 may be used to model the computer-assisted surgical device as if it were attached to the table top even when this is architecturally not the case.

The kinematic model 300 further includes an arm mounting platform coordinate frame 330 that is used as a suitable model for a shared coordinate frame associated with the most proximal points on the articulated arms of the computer-assisted device. In some embodiments, the arm mounting platform coordinate frame 330 may be associated with and oriented relative to a convenient point on an arm mounting platform, such as the arm mounting platform 227. In some examples, the center point of the arm mounting platform coordinate frame 330 may be located on the arm mounting platform orientation axis 236 with the z-axis of the arm mounting platform coordinate frame 330 being aligned with arm mounting platform orientation axis 236. In some examples, a device base to arm mounting platform coordinate transform 335 is used to map positions and/or orientations between the device base coordinate frame 320 and the arm mounting platform coordinate frame 330. In some examples, one or more kinematic models of the links and joints of the computer-assisted device between the device base and the arm mounting platform, such as the set-up structure 220, along with past and/or current joint sensor readings are used to determine the device base to arm mounting platform coordinate transform 335. In some examples consistent with the embodiments of FIG. 2, the device base to arm mounting platform coordinate transform 335 may model the composite effect of the two-part column, shoulder joint, two-part boom, and wrist joint of the setup structure portion of the computer-assisted device.

The kinematic model 300 further includes a series of coordinate frames and transforms associated with each of the articulated arms of the computer-assisted device. As shown in FIG. 3, the kinematic model 300 includes coordinate frames and transforms for three articulated arms, although one of ordinary skill would understand that different computer-assisted devices may include fewer and/or more articulated arms (e.g., one, two, four, five, or more). Consistent with the configuration of the links and joints of the computer-assisted device 210 of FIG. 2, each of the articulated arms is modeled using a manipulator mount coordinate frame, a remote center of motion coordinate frame, and an instrument or camera coordinate frame, depending on a type of instrument mounted to the distal end of the articulated arm.

In the kinematic model 300, the kinematic relationships of a first one of the articulated arms is captured using a manipulator mount coordinate frame 341, a remote center of motion coordinate frame 342, an instrument coordinate frame 343, an arm mounting platform to manipulator mount transform 344, a manipulator mount to remote center of motion transform 345, and a remote center of motion to instrument transform 346. The manipulator mount coordinate frame 341 represents a suitable model for representing positions and/or orientations associated with a manipulator, such as manipulator 260. The manipulator mount coordinate frame 341 is associated with a manipulator mount, such as the manipulator mount 262 of the corresponding articulated arm. The arm mounting platform to manipulator mount transform 344 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 342 is associated with a remote center of motion of the instrument mounted on the manipulator, such as the corresponding remote center of motion 274 of the corresponding manipulator 260. The manipulator mount to remote center of motion transform 345 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the manipulator mount to remote center of motion transform 345 includes an essentially static translational component that does not change as the manipulator and instrument are operated and a dynamic rotational component that changes as the manipulator and instrument are operated.

The instrument coordinate frame 343 is associated with an end effector located at the distal end of the instrument, such as the corresponding end effector 276. The remote center of motion to instrument transform 346 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 346 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 346 may be constrained to reflect that the insertion axis of the shaft of the instrument passes through the remote center of motion and accounts for rotations of the shaft and the end effector about the axis defined by the shaft.

In the kinematic model 300, the kinematic relationships of a second one of the articulated arms is captured using a manipulator mount coordinate frame 351, a remote center of motion coordinate frame 352, an instrument coordinate frame 353, an arm mounting platform to manipulator mount transform 354, a manipulator mount to remote center of motion transform 355, and a remote center of motion to instrument transform 356. The manipulator mount coordinate frame 351 represents a suitable model for representing positions and/or orientations associated with a manipulator, such as manipulator 260. The manipulator mount coordinate frame 351 is associated with a manipulator mount, such as the manipulator mount 262 of the corresponding articulated arm. The arm mounting platform to manipulator mount transform 354 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 352 is associated with a remote center of motion of the manipulator mounted on the articulated arm, such as the corresponding remote center of motion 274 of the corresponding manipulator 260. The manipulator mount to remote center of motion transform 355 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 355 includes an essentially static translational component that does not change as the manipulator and instrument are operated and a dynamic rotational component that changes as the manipulator and instrument are operated.

The instrument coordinate frame 353 is associated with an end effector located at the distal end of the instrument, such as the corresponding instrument 270 and/or end effector 276. The remote center of motion to instrument transform 356 is then based on one or more kinematic models of the links and joints of the computer-assisted device that move and/or orient the corresponding instrument, end effector, and remote center of motion, along with past and/or current joint sensor readings. In some examples, the remote center of motion to instrument transform 356 accounts for the orientation at which the shaft, such as the corresponding shaft 272, passes through the remote center of motion and the distance to which the shaft is advanced and/or withdrawn relative to the remote center of motion. In some examples, the remote center of motion to instrument transform 356 may be constrained to reflect that the insertion axis of the shaft of the instrument passes through the remote center of motion and accounts for rotations of the shaft and the end effector about the insertion axis defined by the shaft.

In the kinematic model 300, the kinematic relationships of a third one of the articulated arms is captured using a manipulator mount coordinate frame 361, a remote center of motion coordinate frame 362, a camera coordinate frame 363, an arm mounting platform to manipulator mount transform 364, a manipulator mount to remote center of motion transform 365, and a remote center of motion to camera transform 366. The manipulator mount coordinate frame 361 represents a suitable model for representing positions and/or orientations associated with a manipulator, such as manipulator 260. The manipulator mount coordinate frame 361 is associated with a manipulator mount, such as the manipulator mount 262 of the corresponding articulated arm. The arm mounting platform to manipulator mount transform 364 is then based on one or more kinematic models of the links and joints of the computer-assisted device between the arm mounting platform and the corresponding manipulator mount, such as the corresponding set-up joints 240, along with past and/or current joint sensor readings of the corresponding set-up joints 240.

The remote center of motion coordinate frame 362 is associated with a remote center of motion of the manipulator mounted on the articulated arm, such as the corresponding remote center of motion 274 of the corresponding manipulator 260. The manipulator mount to remote center of motion transform 365 is then based on one or more kinematic models of the links and joints of the computer-assisted device between the corresponding manipulator mount and the corresponding remote center of motion, such as the corresponding joints 264, corresponding links 266, and corresponding carriage 268 of the corresponding manipulator 260, along with past and/or current joint sensor readings of the corresponding joints 264. When the corresponding remote center of motion is being maintained in fixed positional relationship to the corresponding manipulator mounts, such as in the embodiments of FIG. 2, the mount to remote center of motion transform 365 includes an essentially static translational component that does not change as the manipulator and instrument are operated and a dynamic rotational component that changes as the manipulator and instrument are operated.

The camera coordinate frame 363 is associated with an imaging device, such an endoscope, mounted on the articulated arm. The remote center of motion to camera transform 366 is then based on one or more kinematic models of the links and joints of the computer-assisted device that move and/or orient the imaging device and the corresponding remote center of motion, along with past and/or current joint sensor readings. In some examples, the remote center of motion to camera transform 366 accounts for the orientation at which the shaft, such as the corresponding shaft 272, passes through the remote center of motion and the distance to which the shaft is advanced and/or withdrawn relative to the remote center of motion. In some examples, the remote center of motion to camera transform 366 may be constrained to reflect that the insertion axis of the shaft of the imaging device passes through the remote center of motion and accounts for rotations of the imaging device about the axis defined by the shaft.

As discussed above and further emphasized here, FIG. 3 is merely an example which should not unduly limit the scope of the claims. One of ordinary skill in the art would recognize many variations, alternatives, and modifications. According to some embodiments, the registration between the surgical table and the computer-assisted device may be determined between the table top coordinate frame 310 and the device base coordinate frame 320 using an alternative registration transform. When the alternative registration transform is used, registration transform 325 is determined by composing the alternative registration transform with the inverse/reverse of the table base to table top transform 315. According to some embodiments, the coordinate frames and/or transforms used to model the computer-assisted device may be arranged differently dependent on the particular configuration of the links and joints of the computer-assisted device, its articulated arms, its end effectors, its manipulators, and/or its instruments. According to some embodiments, the coordinate frames and transforms of the kinematic model 300 may be used to model coordinate frames and transforms associated with one or more virtual instruments and/or virtual cameras. In some examples, the virtual instruments and/or cameras may be associated with previously stored and/or latched instrument positions, projections of instruments and/or cameras due to a motion, reference points defined by a surgeon and/or other personnel, and/or the like.

As described previously, as a computer-assisted system, such as computer-assisted systems 100 and/or 200, is being operated it would be desirable to allow continued control of the instruments and/or end effectors while motion of a surgical table, such as surgical tables 170 and/or 280, is allowed while the instruments are inserted into body openings on the patient. Examples of systems permitting active continuation of a surgical procedure during surgical table motion are shown in U.S. Provisional Patent Application No. 62/134,207 entitled "System and Method for Integrated Surgical Table," which was filed Mar. 17, 2015, and concurrently filed PCT Patent Application No. PCT/US2015/057656 entitled "System and Method for Integrated Surgical Table" and published as WO2016/069648 A1, both of which are hereby incorporated by reference in their entirety. In some examples, this may allow for a less time-consuming procedure as surgical table motion may occur without first having to remove the manipulator-controlled surgical instruments from the patient and undock the manipulators from the cannulas that stay inserted in the patient. In some examples, this allows a surgeon and/or other medical personnel to monitor organ movement while the surgical table motion is occurring to obtain a more optimal surgical table pose. In some examples, this may also permit active continuation of a surgical procedure during surgical table motion.

Figure 4A:
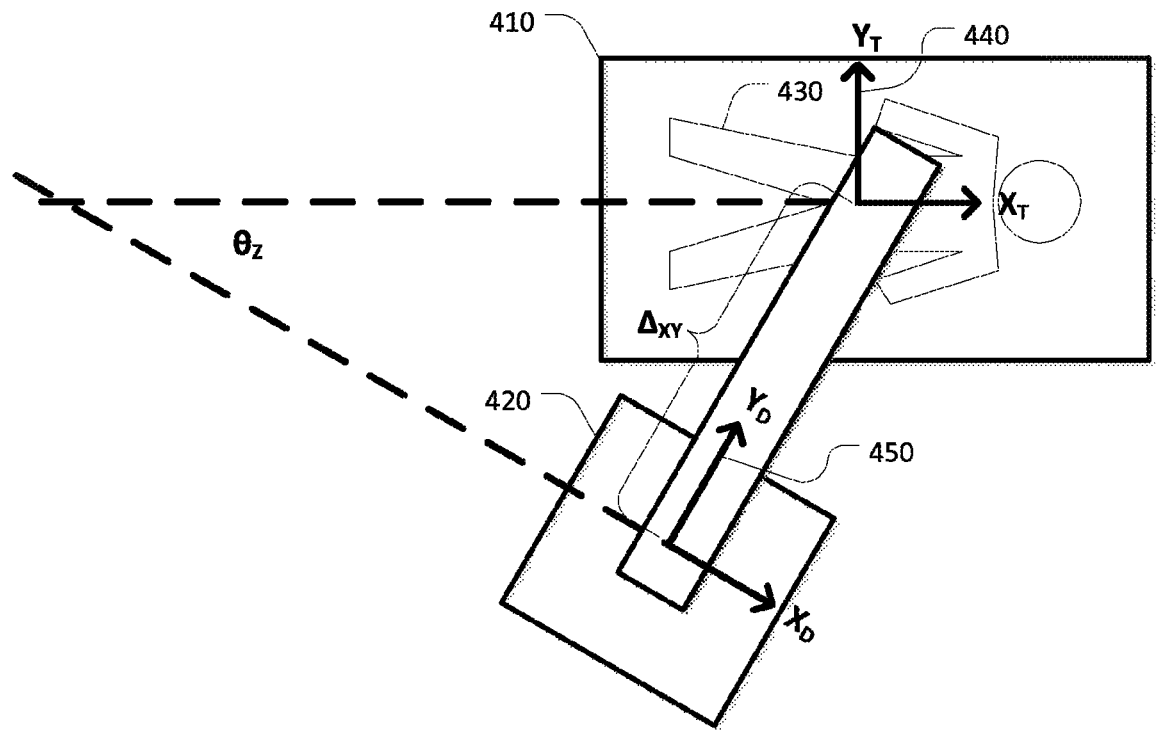
FIGS. 4A and 4B are simplified diagrams of relationships between a surgical table and a computer-assisted device according to some embodiments.
Figure 4B:
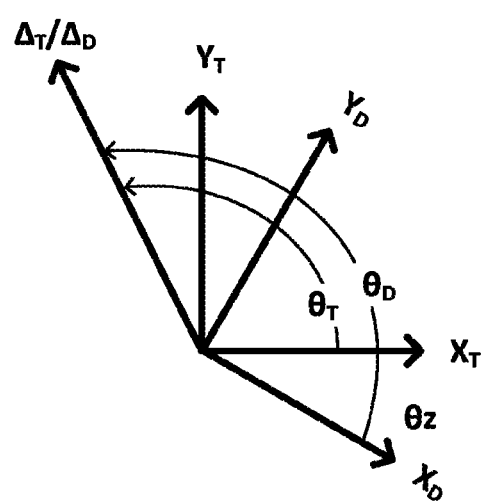

According to some embodiments, it is helpful to know the registration transform 325 between a surgical table and a computer-assisted device so that movement in the patient caused by movement of the top of the surgical table is known by and compensated for by the computer-assisted device. FIGS. 4A and 4B are simplified diagrams of relationships between a surgical table 410 and a computer-assisted device 420 according to some embodiments. In some examples, surgical table 410 may be consistent with surgical table 170 and/or 280 and computer-assisted device may be consistent with computer-assisted device 110, 210, and/or any of the computer-assisted devices of FIGS. 8A-8G. As shown in FIG. 4A, a patient 430 is placed on surgical table 410. Under the assumption that patient 430 is securely strapped to surgical table 410 and one or more portions of the anatomy of patient 430, such as a body opening corresponding to the remote center of motion 274, remain fixed relative to the top of the surgical table 410, any movement in surgical table 410 results in corresponding movement in the one or more portions of the anatomy of patient 430. And although this assumption is somewhat inaccurate, as is discussed in further detail below, by monitoring movements of the top of surgical table 410 in a surgical table coordinate frame and movements of the anatomy of patient 430 in a computer-assisted device coordinate frame, it is possible to determine approximate estimates of the geometric relationship between surgical table 410 and computer-assisted device 420.

Under the assumption that a table base coordinate frame 440 (representatively shown using coordinate axes $X_T$ and $Y_T$) and a device base coordinate frame 450 (representatively shown using coordinate axes $X_D$ and $Y_D$) have a common vertical up or z-axis and the height of the base of the computer-assisted device is known relative to the base of the surgical table, the geometric relationship between surgical table 410 and computer-assisted device 420 may be characterized as determining a horizontal offset and an angular rotation about the vertical up or z axis between surgical table 410 and computer-assisted device 420. This is possible because when table base coordinate frame 440 and device base coordinate frame 450 agree on the z axis, the differences in z coordinate values between table base coordinate frame 440 and device base coordinate frame 450 are already known.

In some examples, table base coordinate frame 440 may correspond to table base coordinate frame 350 and/or device base coordinate frame 450 may correspond to device base coordinate frame 330. In addition, the xy plane of the table base coordinate frame 440 and the xy plane of the device base coordinate frame 450 are parallel. Thus, full registration between surgical table 410 and computer-assisted device 420 involves determining the horizontal offset, $\Delta_{XY}$, between the table base coordinate frame 440 and the device base coordinate frame 450, and the rotation about the z-axis, $\theta_Z$, between the table base coordinate frame 440 and the device base coordinate frame 450. In practice, however, a full registration between surgical table 410 and computer-assisted device 420 may not be needed for operations that involve relative motions between surgical table 410 and computer-assisted device 420, because translations in the table base coordinate frame 440 may be mapped to translations in the device base coordinate frame 450 using $\theta_Z$. In addition, rotations of the top of surgical table 410 relative to the table base coordinate frame 440 may be mapped to rotations in the device base coordinate frame 450 using $\theta_Z$. Thus, a partial registration that determines $\theta_Z$ is often sufficient for most purposes.

FIG. 4B depicts how $\theta_Z$ may be determined by monitoring movement, $\Delta_T$, of the top of surgical table 410 in the table base coordinate frame 440 and movement, $\Delta_D$, of a control point of computer-assisted device 420, such as remote center of motion 274, in the device base coordinate frame 450. As shown in FIG. 4B, the translational differences between the movement of surgical table 410 and computer-assisted device 420 have been removed as they do not affect the angular difference $\theta_Z$ between the two movements. In some examples, the movement $\Delta_T$ may occur as a result of a tilt, Trendelenburg, and/or slide adjustment of surgical table 410. As FIG. 4B demonstrates, the magnitude of $\Delta_T$ and the magnitude of $\Delta_D$ are not as important as knowing the relative directions of $\Delta_T$ and $\Delta_D$ in the xy planes of the table base coordinate frame 440 and the device base coordinate frame 450, respectively. As shown, when a movement $\Delta_T$ of the top of surgical table 410 occurs, a table base to table top transform, such as the table base to table top transform 315, is used to determine an angular direction $\theta_T$ of the movement $\Delta_T$ relative to the $X_T$ axis. Additionally, one or more kinematic models of computer-assisted device 420, such as those depicted in FIG. 3, is used to determine an angular direction $\theta_D$ of a movement $\Delta_D$ of a control point, such as a remote center of motion, relative to the $X_D$ axis. The difference between $\theta_D$ and $\theta_T$ represents the $\theta_Z$ between the table base coordinate frame 440 and the device base coordinate frame 450, which becomes the basis for the registration transform.

Figure 5:
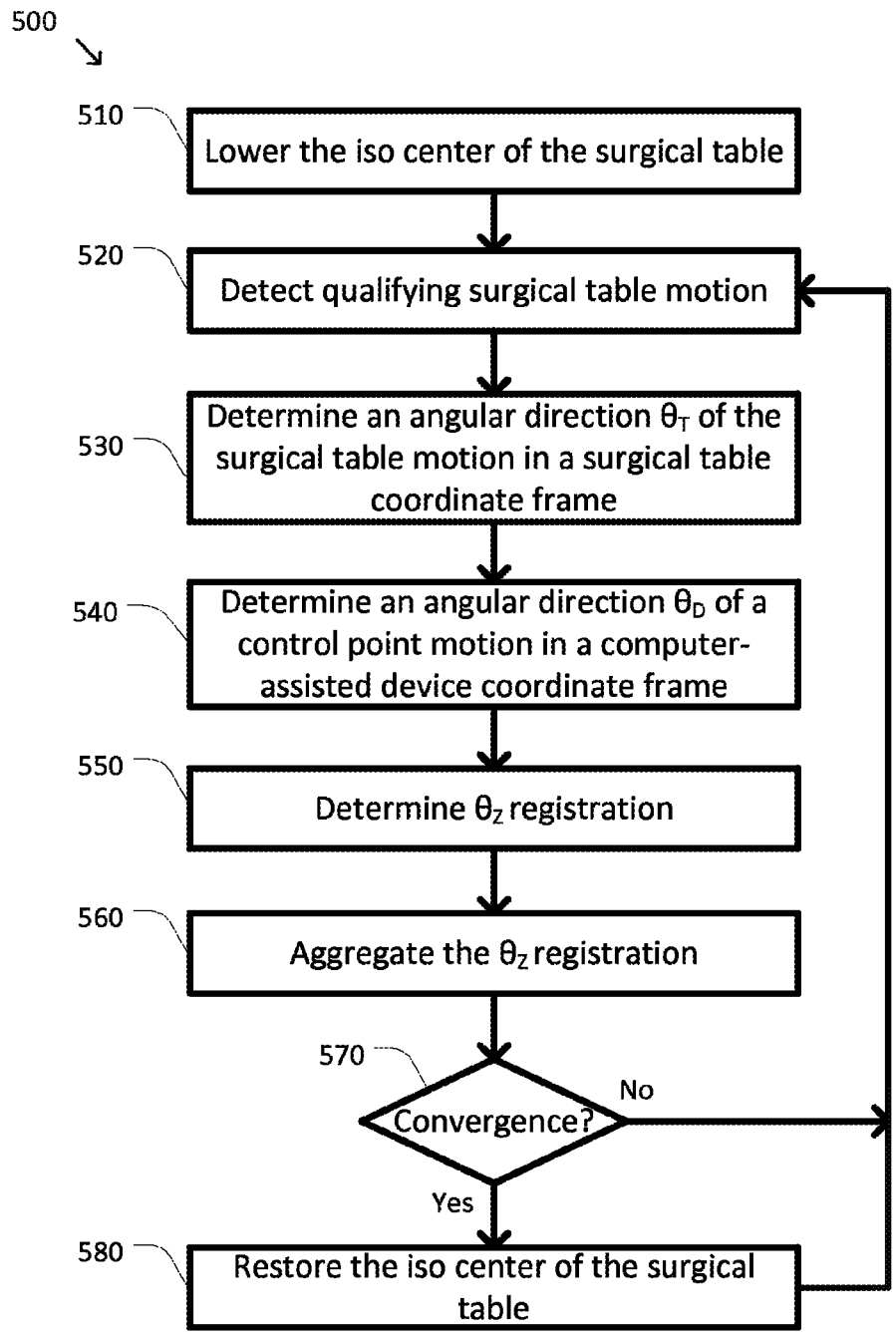
FIG. 5 is a simplified diagram of a method of $\theta_Z$ registering a surgical table with a computer-assisted device according to some embodiments.

FIG. 5 is a simplified diagram of a method 500 of $\theta_Z$ registering a surgical table with a computer-assisted device according to some embodiments. One or more of the processes 510-580 of method 500 may be implemented, at least in part, in the form of executable code stored on non-transient, tangible, machine readable media that when run by one or more processors (e.g., the processor 140 in control unit 130) may cause the one or more processors to perform one or more of the processes 510-580. In some embodiments, method 500 may be used to perform partial registration between the surgical table, such as surgical table 170, 280, and/or 410, and the computer-assisted device, such as computer-assisted device 110, 210, 420, and/or any of the computer-assisted devices of FIGS. 8A-8G. The partial registration may determine a $\theta_Z$ between a table base coordinate frame, such as table base coordinate frame 305 and/or 440, and a device base coordinate frame, such as device base coordinate frame 330 and/or 450. In some embodiments, one or more of the processes 510, 570, and/or 580 are optional and may be omitted.

At an optional process 510, the isocenter of the surgical table is lowered. Because the isocenter of a surgical table, such as isocenter 286, represents an artificially defined point about which at least Trendelenburg rotations occur, it is possible that it may be set at a height that is above one or more control points of the computer-assisted device that are used during method 500. When a control point is located below the isocenter of the surgical table, the movement of the control point is in the opposite direction to the movement of the table top causing an 180° phase shift in angular direction of the movement of the top of the surgical table as determined during process 530. To avoid this problem, the isocenter of the surgical table may be lowered during at least the early portions of the registration of method 500. In some examples, the isocenter of the surgical table may optionally be lowered to a point at or below the top of the surgical table, such as to be coincident with the center of rotation for the tilt axis of the surgical table. In some examples, the isocenter position of the surgical table prior to the lowering is saved for use during process 580. In some examples, lowering the isocenter of the surgical table may also result in enhanced horizontal movement of the top of the table, which may improve the speed at which the registration process converges.

At a process 520, qualifying motion of the surgical table is detected. Not all movement of a control point, such as a remote center of motion, of the computer-assisted device are suitable for use during the registration of method 500. In some examples, vertical movement of the surgical table, which does not generate any horizontal movement, does not provide suitable information for use during method 500. In some examples, there may be small oscillations in the horizontal movement of the control points that do not occur as a result of the surgical table movement. In some examples, these small oscillations may occur as a result of autonomic motions of the patient (e.g., breathing, heartbeat, etc.), oscillations and/or vibrations in the articulated arms and/or manipulators of the computer-assisted device, changes in insufflation, and/or the like. In order to reduce the impact that these oscillations and other errors, such as sensor errors, may introduce into the registration, registration may be limited to qualifying motions. In some examples, a qualifying motion is a net horizontal motion in a control point that exceeds a threshold value determined based on likely oscillations that may occur. In some examples, the threshold value is about 8 to 10 mm or so. In some examples, the qualifying motion is detected by latching and/or storing an initial horizontal position of the control point and then periodically monitoring the actual horizontal position of the control point and waiting until a distance between the actual horizontal position and the initial horizontal position exceeds the threshold value. Once the qualifying motion is detected it is used as a basis for a registration estimate.

In some embodiments, a coherence check may also be used to determine whether the net horizontal motion is a qualifying motion. In some examples, as process 520 periodically monitors the actual horizontal position of the control point, it may record a sequence of incremental motions or vectors indicating the incremental change in the actual horizontal position of the control point between successive instances in which the actual horizontal position of the control point is monitored. In some examples, each of the incremental motions may be longer than a predetermined length, such as 1 mm. In some examples, each of the incremental motions may be a net motion of the control point over a predetermined length of time, such as 10 ms. In some examples, the net horizontal motion is compared against a path of motion described by the incremental motions to determine whether the net horizontal motion is an accurate approximation of the incremental motions. In some examples, the angular components of the incremental motions is compared to the angular components of the net horizontal motion to determine whether there is a consistent direction of motion. In some examples, a length of the path is compared to a magnitude of the net horizontal motion to determine whether there is a consistent pattern of motion. In some examples, a magnitude of a vector sum of the recorded vectors (i.e., a magnitude of the net horizontal motion) is compared to a sum of the magnitudes of each of the recorded vectors. In some examples, when the magnitude of the vector sum of the recorded vectors and the sum of the magnitudes of each of the vectors are within a configurable percentage of each other, such as 90 percent, the net horizontal motion is a qualifying motion. In some examples, Equation 1 is used to perform the coherence test, where $\vec{v}_i$ represents a respective instance of a recorded vector.

$$\frac{|\sum \vec{v}_i|}{\sum |\vec{v}_i|} \geq \text{Configurable\_Threshold} \qquad \text{Equation 1}$$

In some examples, information about the surgical table motion is exchanged between the surgical table and the computer-assisted device. In some examples, the surgical table motion is characterized using a table base to table top transform, such as table base to table top transform 315. In some examples, the surgical table provides the current table base to table top transform to the computer-assisted device. In some examples, the surgical table provides a difference (or delta) between the current table base to table top transform since the last time the table base to table top transform was provided. In some examples, the surgical table provides the current positions and/or velocities of the joints in the articulated structure of the surgical table so that the computer-assisted device may determine the current table base to table top transform using one or more kinematic models of the articulated structure of the surgical table. In some examples, the surgical table sends one or more messages to the computer-assisted device to exchange the table base to table top transform, the delta table base to table top transform, the current joint positions, and/or current joint velocities.

At a process 530, an angular direction $\theta_T$ of the surgical table motion is determined in a surgical table coordinate frame. In some examples, the angular direction $\theta_T$ of the surgical table motion is determined in the surgical table coordinate frame by monitoring the table base to table top transform. In some examples, two versions of the table base to table top transform is used, a latched and/or saved version taken at the start of the qualifying motion detected during process 520 and a latched and/or saved version taken at the end of the qualifying motion detected during process 520. In some examples, differences between the two table base to table top transforms is used to determine the angular direction $\theta_T$. In some examples, the two table base to table top transforms are used to determine a beginning and ending horizontal position of an arbitrary point with the difference between the beginning and ending horizontal positions being used to determine the angular direction $\theta_T$ using trigonometry.

At a process 540, an angular direction $\theta_D$ of a control point motion is determined in a computer-assisted device coordinate frame. In some examples, the angular direction $\theta_D$ of the control point motion is determined in the computer-assisted device coordinate frame by monitoring the movement of the control point in the computer-assisted device coordinate frame. In some examples, the two horizontal positions of the control point taken at the beginning and the end of the qualifying motion detected during process 520 may be used to determine the angular direction $\theta_D$ using trigonometry.

At a process 550, the $\theta_Z$ registration is determined. In some examples, the $\theta_Z$ registration is determined by taking an angular difference between the angular direction $\theta_D$ of the control point determined during process 540 and the angular direction $\theta_T$ of the surgical table determined during process 530.

At a process 560, the $\theta_Z$ registration is aggregated. As discussed above with respect to process 520, the oscillations and/or other errors may introduce inaccuracies in the $\theta_Z$ registration during process 550. To help reduce these inaccuracies, the $\theta_Z$ registration is aggregated with other $\theta_Z$ registration values in order to determine a composite $\theta_Z$ registration value. In some examples, the other $\theta_Z$ registration values may optionally be associated with other control points of the computer-assisted device, such as other remote centers of motion. In some examples, the other $\theta_Z$ registration values may optionally be associated with a sequence of qualifying motions for the same control point and/or the other control points. In this way, the composite $\theta_Z$ registration is continually updated over time. In some examples, the $\theta_Z$ registrations may be aggregated using an averaging function. In some examples, the $\theta_Z$ registrations may be aggregated using exponential smoothing to provide greater emphasis on later obtained $\theta_Z$ registration values. In some examples, randomness reducing processes, such as Kalman filtering and/or other least squares estimators, may optionally be used to aggregate the $\theta_Z$ registration values.

At an optional process 570, it is determined whether the composite $\theta_Z$ registration has converged. As the composite $\theta_Z$ registration is aggregated during process 560, it is monitored to determine whether the composite $\theta_Z$ registration is converged to a reasonably stable value. In some examples, the composite $\theta_Z$ registration is considered converged when incremental changes to the composite $\theta_Z$ registration, as new $\theta_Z$ registration values are determined, are below a threshold, such as 1 to 10 degrees (e.g., 2 degrees). When the composite $\theta_Z$ registration is not converged, additional $\theta_Z$ registration values are determined by repeating processes 520 to 560. When the composite $\theta_Z$ registration is converged, the isocenter is restored using a process 580.

At an optional process 580, the isocenter of the surgical table is restored. The position of the isocenter of the surgical table is restored to the position of the isocenter saved during process 510. After the position of the isocenter is restored, processes 520-560 are repeated to further refine the composite $\theta_Z$ registration. In some examples, however, after restoring the isocenter of the surgical table, process 520 may be altered so that motions associated with Trendelenburg adjustments are no longer qualifying motions. In this way, issues associated with the 180° phase shift may be avoided while still using Trendelenburg adjustments to determine early values for the composite $\theta_Z$ registration.

Figure 6:
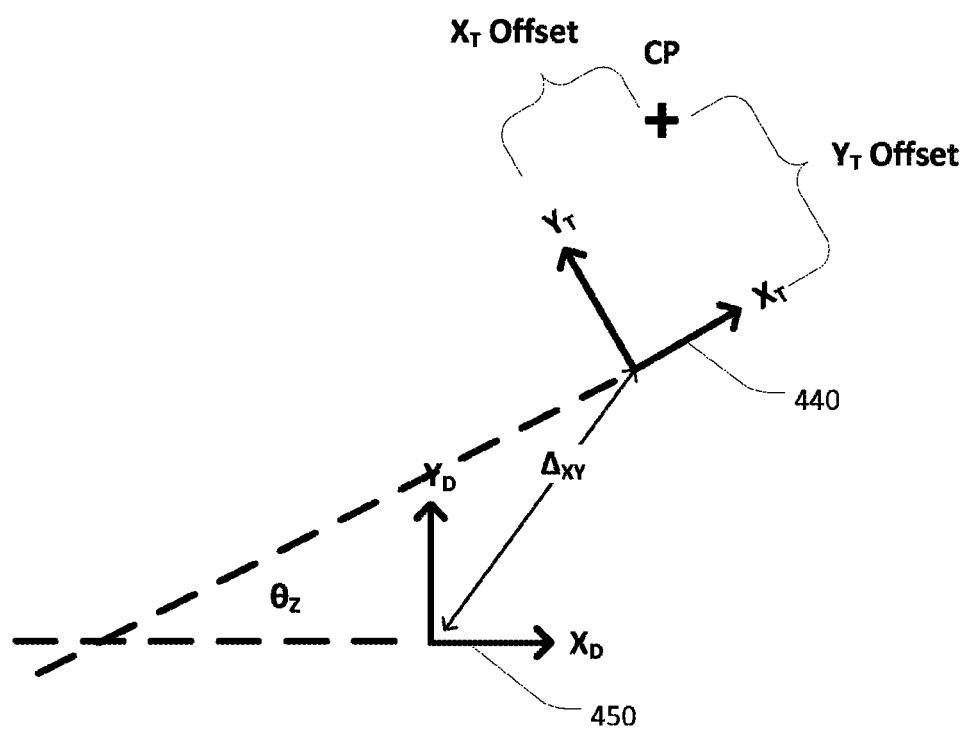
FIG. 6 is a simplified diagram of relationships between a device base coordinate frame and a table base coordinate frame according to some embodiments.

FIG. 6 is a simplified diagram of relationships between the device base coordinate frame 450 and the table base coordinate frame 440 according to some embodiments. As shown in FIG. 6, the relationships between the device base coordinate frame 450 and the table base coordinate frame 440 are reoriented relative to the device base coordinate frame 450 and projected in the XY plane. FIG. 6 further depicts how $\Delta_{XY}$ may be determined by observing tilt and/or Trendelenburg motions in the surgical table and the resulting movement of a control point, such as a remote center of motion of one of the docked articulated arms. Under the assumption that a suitably selected control point on an articulated arm, such as a remote center of motion, is located at a fixed position relative to the top of the surgical table (a reasonable assumption when the remote center of motion is fixed to the anatomy of the patient at a body opening), motions to the control point due to tilt and/or Trendelenburg rotations may be modeled as a rotation about a known point. In some examples, the known point may correspond to a pivot center for the tilt of the surgical table and/or the isocenter for the surgical table. In some examples, the known point is located at an XY center of the table base coordinate frame 450. As shown in Equation 2, when the angular velocity change of the tilt and/or Trendelenburg rotation is $\vec{\Delta}_\theta$ and the geometric relationship in the XY plane between the known point and the control point is $\vec{R}$, the velocity/change in position of the control point may be modeled as $\vec{\Delta}_{CP}$ via the vector cross product.

$$\vec{\Delta}_{CP} = \vec{\Delta}_\theta \times \vec{R} \quad \text{Equation 2}$$

In some examples, the position and movement of the control point is known by the computer-assisted device using the kinematic models of the articulated arm and/or manipulator associated with the control point and the angular velocity of the rotation is known from the surgical table. This leaves $\vec{R}$ as the unknown in Equation 2. Unfortunately, the cross product of Equation 2 is not invertible, so a partial determination of $\vec{R}$ may be inferred by determining the shortest distance or offset between the control point and the axis of rotation as shown in Equation 3.

$$\text{offset} = \frac{\vec{\Delta}_{CP} \times \vec{\Delta}_\theta}{\|\vec{\Delta}_\theta\|^2} \quad \text{Equation 3}$$

Based on the surgical table orientations shown in FIG. 4, tilt rotations occur about the $X_T$ axis and horizontal projections of Trendelenburg rotations occur about the $Y_T$ axis. Thus, a tilt rotation that results in a movement of the control point in the $Y_T$ direction may be used to determine a $Y_T$ offset of the control point relative to the fixed point, and a Trendelenburg rotation that results in a in a movement of the control point in the $X_T$ direction may be used to determine a $X_T$ offset of the control point relative to the fixed point. This combined with previous knowledge of $\theta_Z$ from method 500 are used to project the $X_T$ and $Y_T$ offsets along the $X_T$ and $Y_T$ axes relative to the known position of the control point to determine the XY center of the table base coordinate frame 440, and thus $\Delta_{XY}$. In some examples, the computations of Equation 3 may be simplified by working with projections of the various vectors in the XY plane.

Figure 7:
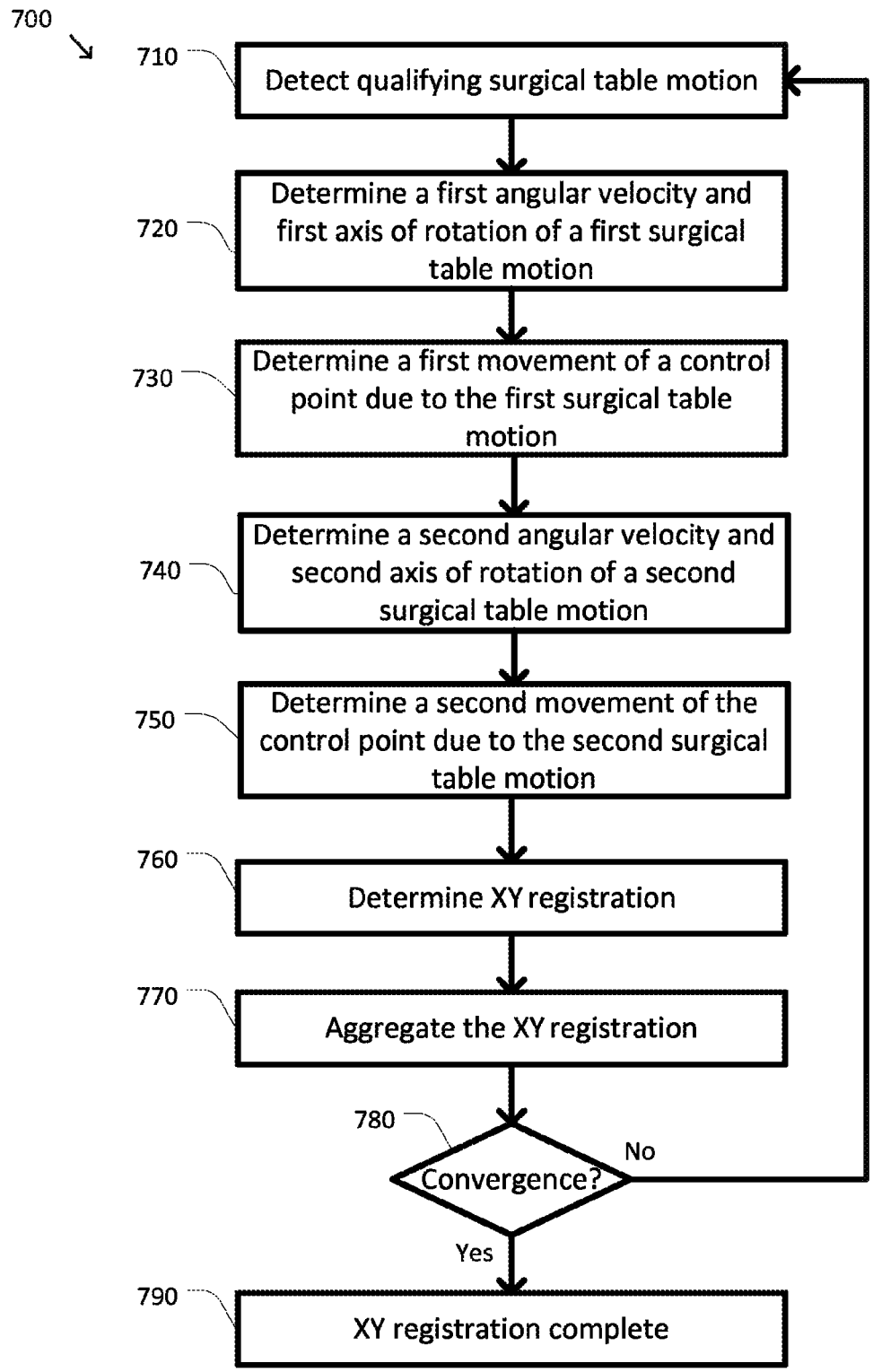
FIG. 7 is a simplified diagram of a method of XY registering a surgical table with a computer-assisted device according to some embodiments.

FIG. 7 is a simplified diagram of a method 700 of XY registering a surgical table with a computer-assisted device according to some embodiments. One or more of the processes 710-790 of method 700 may be implemented, at least in part, in the form of executable code stored on non-transient, tangible, machine readable media that when run by one or more processors (e.g., the processor 140 in control unit 130) may cause the one or more processors to perform one or more of the processes 710-790. In some embodiments, method 700 may be used to perform partial registration between the surgical table, such as surgical table 170, 280, and/or 410, and the computer-assisted device, such as computer-assisted device 110, 210, 420, and/or any of the computer-assisted devices of FIGS. 8A-8G. The partial registration may determine $\Delta_{XY}$ between a table base coordinate frame, such as table base coordinate frame 305 and/or 440, and a device base coordinate frame, such as device base coordinate frame 330 and/or 450.

At a process 710, qualifying motion of the surgical table is detected. Not all movement of a control point, such as a remote center of motion, of the computer-assisted device are suitable for use during the registration of method 700. In some examples, a qualifying motion may be a horizontal movement in the control point due to a tilt rotation or a horizontal movement in the control point due to a Trendelenburg rotation. In some examples, the qualifying motion may be determined as a net horizontal motion $\vec{\Delta}_{CP}$ or as a velocity of the control point. In some embodiments, the net horizontal motion or the velocity may be low-pass filtered to reduce the effects of vibrations and/or the like in the control point due to motion sources other than surgical table motion. In some examples, motion length thresholds and/or coherence checks, similar to those performed during process 520, may also be used to determine whether a net horizontal motion is a qualifying motion.

At a process 720, a first angular velocity and a first axis of rotation of a first surgical table motion is determined. In some examples, the first angular velocity and the first axis of rotation define a first rotation vector $\vec{\Delta}_{\theta 1}$. In some examples, the first angular velocity and the first axis of rotation are determined from one or more messages exchanged between the surgical table and the computer-assisted surgical device describing whether the first surgical table motion is a tilt rotation or a Trendelenburg rotation and the amount of the tilt and/or Trendelenburg rotation. In some examples, when the first surgical table motion is a tilt rotation the first axis of rotation is the $X_T$ axis and when the first surgical table motion is a Trendelenburg rotation the first axis of rotation is the $Y_T$ axis as shown in the examples of FIG. 6.

At a process 730, a first movement of the control point due to the first surgical table position is determined. By monitoring the velocity of the control point and/or a change in the position of the control point, a first movement of the control point $\vec{\Delta}_{CP1}$ is determined. In some examples, kinematic models of the corresponding articulated arm and/or manipulator along with joint sensor readings are used to determine the first movement of the control point $\vec{\Delta}_{CP1}$.

At a process 740, a second angular velocity and a second axis of rotation of a second surgical table motion is determined. The second axis of rotation is different from the first axis of rotation. In some examples, the second angular velocity and the second axis of rotation define a second rotation vector $\vec{\Delta}_{\theta 2}$. In some examples, the second angular velocity and the second axis of rotation are determined from one or more messages exchanged between the surgical table and the computer-assisted surgical device describing whether the second surgical table motion is a tilt rotation or a Trendelenburg rotation and the amount of the tilt and/or Trendelenburg rotation. In some examples, when the second surgical table motion is a tilt rotation the second axis of rotation is the $X_T$ axis and when the second surgical table motion is a Trendelenburg rotation the second axis of rotation is the $Y_T$ axis as shown in the examples of FIG. 6.

At a process 750, a second movement of the control point due to the second surgical table position is determined. By monitoring the velocity of the control point and/or a change in the position of the control point, a second movement of the control point $\vec{\Delta}_{CP2}$ is determined. In some examples, kinematic models of the corresponding articulated arm and/or manipulator along with joint sensor readings are used to determine the second movement of the control point $\vec{\Delta}_{CP2}$.

At a process 760, the XY registration is determined. In some examples, the XY registration is determined by first applying Equation 3 using the first rotation vector $\vec{\Delta}_{\theta 1}$ and the first control point movement $\vec{\Delta}_{CP1}$ determined during processes 720 and 730 to determine a first offset and then applying Equation 3 using the second rotation vector $\vec{\Delta}_{\theta 2}$ and the second control point movement $\vec{\Delta}_{CP2}$ determined during processes 740 and 750 to determine a second offset. Because the first and second rotation axes are different, the first and second offsets may be projected perpendicular to the respective axes of rotation and relative to the position of the control point to determine the XY registration in the form of $\Delta_{XY}$. In some examples, the directions along which to project the first and second offsets relative to the position of the control point are determined based on the $\theta_Z$ registration of method 500. In the examples of FIG. 6, when the first and second rotation axes correspond to the $X_T$ and $Y_T$ axes, respectively, the first and second offsets correspond to the $Y_T$ and $X_T$ offsets, respectively. In some examples, the $Y_T$ and $X_T$ offsets are projected along the $Y_T$ and $X_T$ axes, respectively. In some examples, the orientations of the $Y_T$ and $X_T$ axes are known relative to the device coordinate frame 450 due to the $\theta_Z$ registration. In some examples, projections of $\vec{\Delta}_{CP1}$ and $\vec{\Delta}_{CP2}$ in the XY plane may optionally be used.

At a process 770, the XY registration is aggregated. To help reduce inaccuracies in the XY registration and/or to improve the XY registration, the XY registration is aggregated with other XY registration values in order to determine a composite XY registration value. In some examples, the other XY registration values may optionally be associated with other control points of the computer-assisted device, such as other remote centers of motion. In some examples, the other XY registration values may optionally be associated with a sequence of first and/or second movements for the same control point and/or the other control points. In this way, the composite XY registration is continually updated over time. In some examples, the XY registrations may be aggregated using an averaging function. In some examples, the XY registrations may be aggregated using exponential smoothing to provide greater emphasis on later obtained XY registration values. In some examples, randomness reducing processes, such as Kalman filtering and/or other least squares estimators, may optionally be used to aggregate the XY registration values.

At an optional process 780, it is determined whether the composite XY registration has converged. As the composite XY registration is aggregated during process 770, it is monitored to determine whether the composite XY registration is converged to a reasonably stable value. In some examples, the composite XY registration is considered converged when incremental changes to the composite XY registration, as new XY registration values are determined, are below a threshold, such as 20 to 40 mm (e.g., 30 mm). When the composite XY registration is not converged, additional XY registration values are determined by repeating processes 710 to 770. When the composite XY registration is converged, the XY registration completes using a process 790 and the XY registration is made available for other control algorithms of the computer-assisted device.

As discussed above and further emphasized here, FIGS. 5 and 7 are merely examples which should not unduly limit the scope of the claims. One of ordinary skill in the art would recognize many variations, alternatives, and modifications. According to some embodiments, rather than lowering and restoring the isocenter of the surgical table during processes 510 and 580, respectively, additional information about the control points and the isocenter may optionally be used to account for any possible 180° degree phase shift in the determination of the angular direction $\theta_T$ of the surgical table motion. In some examples, a height of the isocenter in the table base coordinate frame is compared to a height of the control point in the device base coordinate frame and when the height of the control point is below the height of the isocenter, the value of $\theta_T$ is corrected by 180°. In some examples, the 180° correction is applied whenever a center of rotation of the motion in the surgical table is located above the control point.

According to some embodiments, aggregations of the net motion of the control points of different articulated arms may optionally be used as the net motions determined during processes 520, 730, and/or 750. In some examples, when multiple articulated arms are docked to the patient, the net motions of one or more control points of each of the articulated arms is aggregated to determine the net motions used in other processes of methods 500 and/or 700. In some examples, because the geometric relationships between the control points of different articulated arms are mostly fixed relative to each other due to the anatomy of the patient, the qualifying surgical table motion affects each of the control points similarly. In some examples, the aggregation of the net motions of the control points is used to determine when a qualifying surgical table motion takes place during processes 520 and/or 720. In some examples, the aggregation of the net motions from the control points is used to determine an aggregate angular direction $\theta_D$ of the control points during process 540, which is then used to determine $\theta_Z$ during process 550. In some examples, the aggregation of the net motions from the control points is used to determine an aggregate first and/or second movement of the control point during processes 730 and/or 750, which is then used to determine the XY registration during process 770.

In some examples, the aggregations may optionally be determined using an averaging function, exponential smoothing, Kalman filtering, least squares estimators, and/or the like. In some examples, when the aggregations based on the multiple control points occur earlier in methods 500 and/or 700, this may simplifies the aggregations performed during processes 560 and/or 570. In some examples, when the aggregations of the net motions of the multiple control points are consistent with each of the net motions of the individual control points, the convergence tests of processes 570 and/or 780 may optionally be eliminated. In some examples, the net motions of the individual control points may be consistent with the aggregation of the net motion when there is no more than a threshold difference between each of the net motions of the individual control points and the aggregation of the net motion. In some examples, the threshold difference is ten percent or less.

According to some embodiments, the qualified motions used during method 500 and/or 700 to perform the registration, may be generated in different ways. In some examples, the qualified motions may occur as a result of a sequence of one or more test and/or registration motions of the surgical table that may, for example, be requested by computer-assisted device. In some examples, the sequence of test motions is selected to achieve rapid convergence in the determination of $\theta_Z$ and/or $\Delta_{XY}$. In some examples, the qualified motions occur as a result of monitoring surgical table motion selected by medical personnel to position the surgical table and/or the patient during a procedure.

According to some embodiments, variations on the first and second axes of rotation may optionally be used for method 700. In some examples, the first and second axes of rotation may be other than the $X_T$ and $Y_T$ axes. In some examples, method 700 is used to determine the XY registration as long as the first and second axes of rotation are at least a suitable angular distance apart (e.g., 30 degrees) and the orientations between the first and second axes and the device base coordinate frame is known. In some examples, the order in which the first and second surgical table motions occur is flexible. In some examples, a tilt rotation may be used before a Trendelenburg rotation and/or a Trendelenburg rotation may be used before a tilt rotation.

According to some embodiments, method 700 may be used to perform a partial XY registration that addresses either a tilt registration or a Trendelenburg registration. In some examples, method 700 may be modified to separately determine and/or aggregate an offset derived from tilt rotations and an offset derived from Trendelenburg rotations. In some examples, the separate offsets derived from tilt and Trendelenburg rotations are combined to determine the overall XY registration. In some examples, state variables may optionally be used to determine whether one or both of the offsets derived from tilt and Trendelenburg rotations are independently converged.

According to some embodiments, the registrations determined during methods 500 and/or 700 remain valid as long as the base of the surgical table and the base of the computer-assisted device remain fixed relative to each other. In some examples, whenever the base of the surgical table and/or the base of the computer-assisted device move, such as may occur when one or more feet, wheels, and/or mounting clamps are unlocked, methods 500 and/or 700 are repeated to reestablish registration. In some examples, movement of either the base of the surgical table and/or the base of the computer-assisted device may be determined by monitoring sequence numbers sequence numbers tracking the number of times each of the feet, wheel, and mounting clamp locks are engaged and/or disengaged and rotational encoders and/or rotational counters associated with each wheel tracking rotation of any one of the wheels. Changes in any of the sequence numbers provide an indication that movement of the base of the surgical table and/or the base of the computer-assisted device has or is occurring.

In some embodiments, the registration determined during methods 500 and/or 700 remain valid as long as communication is not lost between the surgical table and the computer-assisted device, loss of power in the surgical table and/or the computer-assisted device, a reset in the surgical table and/or the computer-assisted device, and/or the like.

According to some embodiments, method 500 may be terminated and registration considered complete after process 580 is completed.

Some examples of control units, such as control unit 130 may include non-transient, tangible, machine readable media that include executable code that when run by one or more processors (e.g., processor 140) may cause the one or more processors to perform the processes of methods 500 and/or 700. Some common forms of machine readable media that may include the processes of methods 500 and/or 700 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted medical system comprising:
a computer-assisted medical device comprising an articulated arm, the articulated arm configured to have a distally mounted instrument, wherein the distally mounted instrument is configured to be inserted into a patient at a body opening; and
a control unit coupled to the articulated arm;
wherein the control unit is configured to:
detect a first motion of a surgical table coupled to the control unit via a communications connection, the first motion of the surgical table causing a corresponding second motion of a point associated with the articulated arm;
determine a first angular direction of the first motion in a surgical table coordinate frame;
determine a second angular direction of the second motion in a computer-assisted medical device coordinate frame; and
determine a first angular relationship between the surgical table and the computer-assisted medical device based on the first and second angular directions.

2. The system of claim 1, wherein the point associated with the articulated arm corresponds to a remote center of motion of the articulated arm associated with the body opening.

3. The system of claim 1, wherein the control unit is further configured to determine the first angular direction based on a first surgical table transform recorded at a beginning of the first motion and a second surgical table transform at an end of the first motion.

4. The system of claim 1, wherein the control unit is further configured to determine the second angular direction based on a first position of the point associated with the articulated arm at a beginning of the second motion and a second position of the point associated with the articulated arm at an end of the second motion.

5. The system of claim 1, wherein a length of the second motion is greater than a predetermined threshold.

6. The system of claim 1, wherein the second motion comprises a sequence of incremental motions.

7. The system of claim 6, wherein the control unit is further configured to compare the second motion to a path described by the incremental motions.

8. The system of claim 6, wherein the control unit is further configured to:
determine a magnitude of the second motion;
determine a sum of magnitudes of each of the incremental motions; and
determine that a ratio of the magnitude of the second motion and the sum of magnitudes of each of the incremental motions is greater than a predetermined threshold.

9. The system of claim 1, wherein the control unit is configured to determine the second angular direction of the second motion in the computer-assisted medical device coordinate frame based on an aggregation of points associated with multiple articulated arms of the computer-assisted medical device, wherein the points associated with the multiple articulated arms comprises the point associated with the articulated arm, and wherein the multiple articulated arms comprises the articulated arm.

10. The system of claim 1, wherein the control unit is further configured to aggregate the first angular relationship with other angular relationships to form a composite angular relationship, the other angular relationships corresponding to angular relationships between the surgical table and the computer-assisted medical device due to additional surgical table motions.

11. The system of claim 10, wherein the control unit is further configured to continue to aggregate the first angular relationship with the other angular relationships until the composite angular relationship converges.

12. The system of claim 11, wherein the control unit is further configured to lower an isocenter of the surgical table until the composite angular relationship converges.

13. The system of claim 12, wherein the control unit is further configured to restore the isocenter after the composite angular relationship converges, and wherein Trendelenburg adjustments are excluded from the first motion after the isocenter is restored.

14. The system of claim 1, wherein the control unit is further configured to generate a surgical table to computer-assisted medical device transform based on the first angular relationship.

15. The system of claim 1, wherein the control unit lowers an isocenter of the surgical table before detecting the first and second motions.

16. The system of claim 1, wherein the control unit is further configured to determine the first angular relationship based on a difference between the first and second angular directions.

17. The system of claim 1, wherein when a center of rotation of the first motion is located at a height above the point associated with the articulated arm, the control unit adjusts the first angular direction by 180 degrees.

18. The system of claim 17, wherein the center of rotation of the first motion corresponds to an isocenter of the surgical table.

19. The system of claim 1 wherein the control unit is further configured to direct the surgical table to perform the first motion.

20. The system of claim 1, wherein the control unit is further configured to:
detect a third motion of the surgical table, the third motion of the surgical table comprising a first rotation about a first axis, the third motion of the surgical table causing a corresponding fourth motion of the point associated with the articulated arm;
detect a fifth motion of the surgical table, the fifth motion of the surgical table comprising a second rotation about a second axis, the fifth motion of the surgical table causing a corresponding sixth motion of the point associated with the articulated arm, the second axis being different than the first axis;
determine a first perpendicular distance between the point associated with the articulated arm and the first axis based on the first rotation and the fourth motion of the point associated with the articulated arm;
determine a second perpendicular distance between the point associated with the articulated arm and the second axis based on the second rotation and the sixth motion of the point associated with the articulated arm; and
determine an XY registration between the device and the surgical table based on a position of the point associated with the articulated arm and the first and second perpendicular distances.

21. The system of claim 20, wherein the XY registration between the device and the surgical table corresponds to a location of a point of rotation for the surgical table in the computer-assisted medical device coordinate frame.

22. The system of claim 20, wherein the first axis and the second axis have an angular separation of at least 30 degrees.

23. The system of claim 20, wherein the first axis is a tilt rotational axis and the second axis is a Trendelenburg rotational axis.

24. The system of claim 20, wherein the first motion and the third motion are a same motion.

25. The system of claim 20, wherein the fourth and sixth motions are based on aggregations of points associated with multiple articulated arms of the computer-assisted medical system.

26. The system of claim 20, wherein the control unit is further configured to aggregate the XY registration with other XY registrations to form a composite XY registration.

27. The system of claim 20, wherein the third motion is a tilt adjustment and the fifth motion is a Trendelenburg adjustment.

28. A method of registering a surgical table and a computer-assisted medical device, the method comprising:
detecting a first motion of the surgical table, the first motion causing a corresponding second motion of a point associated with an articulated arm of the computer-assisted medical device, the computer-assisted medical device being coupled to the surgical table via a communications connection;
determining a first angular direction of the first motion in a surgical table coordinate frame;
determining a second angular direction of the second motion in a computer-assisted medical device coordinate frame; and determining a first angular relationship between the surgical table and the computer-assisted medical device based on the first and second angular directions.

29. The method of claim 28, wherein the point associated with the articulated arm corresponds to a remote center of motion of the articulated arm.

30. The method of claim 28, wherein:
determining the first angular direction is based on a first surgical table transform and a second surgical table transform, the first surgical table transform being at a beginning of the first motion and the second surgical table transform being at an end of the first motion; and
determining the second angular direction is based on a first position of the point associated with the articulated arm and a second position of the point associated with the articulated arm, the first position of the point associated with the articulated arm being at a beginning of the second motion and the second position of the point associated with the articulated arm being at an end of the second motion.

31. The method of claim 28, wherein determining the second angular direction of the second motion in the computer-assisted medical device coordinate frame comprises using an aggregation of points associated with multiple articulated arms of the computer-assisted medical device, the points associated with the multiple articulated arms comprising the point associated with the articulated arm, and the multiple articulated arms comprising the articulated arm.

32. The method of claim 28, further comprising aggregating the first angular relationship with other angular relationships to form a composite angular relationship.

33. The method of claim 28, further comprising:
detecting a third motion of the surgical table, the third motion of the surgical table comprising a first rotation about a first axis, the third motion of the surgical table causing a corresponding fourth motion of the point associated with the articulated arm;
detecting a fifth motion of the surgical table, the fifth motion of the surgical table comprising a second rotation about a second axis, the fifth motion of the surgical table causing a corresponding sixth motion of the point associated with the articulated arm, the second axis being different than the first axis;
determining a first perpendicular distance between the point associated with the articulated arm and the first axis based on the first rotation and the fourth motion of the point associated with the articulated arm;
determining a second perpendicular distance between the point associated with the articulated arm and the second axis based on the second rotation and the sixth motion of the point associated with the articulated arm; and
determining an XY registration between the device and the surgical table based on a position of the point associated with the articulated arm and the first and second perpendicular distances.

34. The method of claim 33, wherein the fourth and sixth motions are based on aggregations of points associated with multiple articulated arms of the computer-assisted medical device.

* * * * *

UNITED STATES PATENT AND TRADEMARK OFFICE
CERTIFICATE OF CORRECTION

PATENT NO. : 10,555,777 B2
APPLICATION NO. : 15/522180
DATED : February 11, 2020
INVENTOR(S) : Paul G. Griffiths and Brandon D. Itkowitz Page 1 of 1

It is certified that error appears in the above-identified patent and that said Letters Patent is hereby corrected as shown below:

On the Title Page

(56) References Cited, Page 2:
Please insert --2013/0072822    3/2013  Auchinleck et al.--.

Signed and Sealed this
Thirty-first Day of March, 2020

Andrei Iancu
*Director of the United States Patent and Trademark Office*